(12) United States Patent
Greaves et al.

(10) Patent No.: US 7,780,743 B2
(45) Date of Patent: Aug. 24, 2010

(54) FLUORESCENT ENTITY, DYEING COMPOSITION CONTAINING AT LEAST ONE FLUORESCENT ENTITY, AND METHOD FOR LIGHTENING KERATIN MATERIALS USING SAID AT LEAST ONE FLUORESCENT ENTITY

(75) Inventors: Andrew Greaves, Montevrain (FR); Nicolas Daubresse, La Celles St. Cloud (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/293,955

(22) PCT Filed: Mar. 23, 2007

(86) PCT No.: PCT/FR2007/050997

§ 371 (c)(1),
(2), (4) Date: Apr. 1, 2009

(87) PCT Pub. No.: WO2007/110531

PCT Pub. Date: Oct. 4, 2007

(65) Prior Publication Data

US 2009/0320216 A1    Dec. 31, 2009

Related U.S. Application Data

(60) Provisional application No. 60/792,941, filed on Apr. 19, 2006, provisional application No. 60/901,324, filed on Feb. 15, 2007.

(30) Foreign Application Priority Data

Mar. 24, 2006  (FR) .................................. 06 51035
Feb. 5, 2007   (FR) .................................. 07 53076

(51) Int. Cl.
*A61Q 5/10* (2006.01)
*C07D 221/06* (2006.01)

(52) U.S. Cl. ........................ 8/405; 8/426; 8/568; 8/573; 8/587; 8/648; 8/650; 8/652; 546/98

(58) Field of Classification Search .................... 8/405, 8/426, 568, 573, 587, 648, 650, 652; 546/98
See application file for complete search history.

(56) References Cited

U.S. PATENT DOCUMENTS

| | | | |
|---|---|---|---|
| 2,904,385 A | 9/1959 | Roger et al. | |
| 4,823,985 A | 4/1989 | Grollier et al. | |
| 7,147,673 B2 | 12/2006 | Plos et al. | |
| 7,150,764 B2 | 12/2006 | Plos et al. | |
| 7,186,278 B2 | 3/2007 | Plos et al. | |
| 7,192,454 B2 | 3/2007 | Plos et al. | |
| 7,195,650 B2 | 3/2007 | Plos et al. | |
| 7,195,651 B2 | 3/2007 | Plos et al. | |
| 7,198,650 B2 | 4/2007 | Pourille-Grethen et al. | |
| 7,204,860 B2 | 4/2007 | Plos et al. | |
| 7,208,018 B2 | 4/2007 | Gourlaouen et al. | |
| 7,217,296 B2 | 5/2007 | Pastore et al. | |
| 7,250,064 B2 | 7/2007 | Plos et al. | |
| 7,261,744 B2 | 8/2007 | Gourlaouen et al. | |
| 7,276,086 B2 | 10/2007 | Gourlaouen | |
| 7,303,589 B2 | 12/2007 | Greaves et al. | |
| 7,377,946 B2 | 5/2008 | Gourlaouen et al. | |
| 7,488,354 B2 | 2/2009 | Daubress et al. | |
| 7,531,008 B2 | 5/2009 | Lagrange | |
| 7,544,215 B2 | 6/2009 | Speckbacher et al. | |
| 2003/0176316 A1 | 9/2003 | Whitehead et al. | |
| 2004/0253757 A1 | 12/2004 | Gourlaouen et al. | |
| 2005/0031563 A1 | 2/2005 | Gourlaouen et al. | |
| 2006/0182751 A1* | 8/2006 | Gazzard et al. | 424/178.1 |
| 2007/0231940 A1 | 10/2007 | Gourlaouen et al. | |
| 2009/0049621 A1 | 2/2009 | Greaves et al. | |
| 2009/0089939 A1 | 4/2009 | Greaves et al. | |
| 2009/0126125 A1 | 5/2009 | Greaves et al. | |
| 2009/0126755 A1 | 5/2009 | Guerin et al. | |

FOREIGN PATENT DOCUMENTS

| | | |
|---|---|---|
| BE | 669 934 | 1/1966 |
| EP | 0 860 636 | 8/1998 |
| EP | 1 464 321 | 10/2004 |
| EP | 1 464 323 | 10/2004 |
| EP | 1 464 324 | 10/2004 |
| EP | 1 647 580 | 4/2006 |
| EP | 1 792 605 | 6/2007 |

(Continued)

OTHER PUBLICATIONS

STIC Search Report dated Feb. 2, 2010.*

(Continued)

*Primary Examiner*—Eisa B Elhilo
(74) *Attorney, Agent, or Firm*—Finnegan, Henderson, Farabow, Garrett & Dunner L.L.P.

(57) ABSTRACT

The invention relates to the dyeing of keratin materials using naphthylimide thiol/disulphide thiol fluorescent dyes, and to a dyeing process which has a lightening effect on keratin materials, in particular keratin fibres, especially human keratin fibres such as the hair, using said composition. It similarly relates to novel thiol/disulphide fluorescent dyes and to uses thereof in lightening keratin materials.

This composition makes it possible to obtain a particularly resistant and visible lightening effect on dark keratin fibres.

23 Claims, 1 Drawing Sheet

FOREIGN PATENT DOCUMENTS

| | | |
|---|---|---|
| EP | 2 001 960 | 12/2008 |
| EP | 2 004 757 | 12/2008 |
| EP | 2 018 847 | 1/2009 |
| EP | 2 062 945 | 5/2009 |
| FR | 1 156 407 | 5/1958 |
| FR | 2 586 913 | 3/1987 |
| FR | 2 830 189 | 4/2003 |
| FR | 2 830 194 | 4/2003 |
| FR | 2 850 271 | 7/2004 |
| FR | 2 921 381 | 3/2009 |
| FR | 2 921 377 | 6/2009 |
| GB | 2 143 541 | 2/1985 |
| GB | 2 180 215 | 3/1987 |
| WO | WO 96/41173 | 12/1996 |
| WO | WO 99/51194 | 10/1999 |
| WO | WO 03/028685 | 4/2003 |
| WO | WO 2004/091473 | 10/2004 |
| WO | WO 2004/091556 | 10/2004 |
| WO | WO 2005/004822 | 1/2005 |
| WO | WO 2005/075574 | 8/2005 |
| WO | WO 2005/097051 | 10/2005 |
| WO | WO 2006/060533 | 6/2006 |
| WO | WO 2006/134043 | 12/2006 |
| WO | WO 2006/136617 | 12/2006 |
| WO | WO 2007/025889 | 3/2007 |
| WO | WO 2007/039527 | 4/2007 |
| WO | WO 2007/110537 | 10/2007 |
| WO | WO 2007/110539 | 10/2007 |
| WO | WO 2007/110542 | 10/2007 |
| WO | WO 2009/037324 | 3/2009 |
| WO | WO 2009/037348 | 3/2009 |
| WO | WO 2009/037350 | 3/2009 |
| WO | WO 2009/037385 | 3/2009 |
| WO | WO 2009/040354 | 4/2009 |
| WO | WO 2009/040355 | 4/2009 |

OTHER PUBLICATIONS

Ashwell, G. et al., "Improved Molecular Rectification from Self-Assembled Monolayers of a Sterically Hindered Dye," Journal of the American Chemical Society, vol. 127, No. 46, (2005), pp. 16238-16244.

Ashwell, G. et al., "Induced Rectification from Self-Assembled Monolayers of Sterically Hindered-Bridged Chromophores," Journal of Materials Chemistry, vol. 15, No. 11, (2005), pp. 1160-1166.

Ashwell, G. et al., "Molecular Rectification: Self-Assembled Monolayers of a Donor Acceptor Chromophore Connected via a Truncated Bridge," Journal of Materials Chemistry, vol. 13, No. 12, (2003), pp. 2855-2857.

Copending U.S. Appl. No. 12/293,684, filed Sep. 19, 2008.
Copending U.S. Appl. No. 12/293,723, filed Sep. 19, 2008.
Copending U.S. Appl. No. 12/293,955, filed Sep. 22, 2008.
English language Abstract of EP 1 464 323 from esp@cenet, (2004).
English language Abstract of FR 2 921 377 from esp@cenet, (2009).
English language Abstract of FR 2 921 381 from esp@cenet, (2009).
International Search Report for PCT/FR2007/050997, dated Jun. 19, 2008, (corresponding to the present case).
International Search Report for PCT/FR2007/051003, dated Feb. 19, 2008, (corresponding to co-pending U.S. Appl. No. 12/293,723).
International Search Report for PCT/FR2007/051005, dated May 6, 2008, (corresponding to co-pending U.S. Appl. No. 12/293,684).
International Search Report for PCT/FR2007/051008, dated Feb. 5, 2008, (corresponding to co-pending U.S. Appl. No. 12/282,586).

Kajikawa, K. et al., "Preparation and Optical Characterization of Hemicyanine Self-Assembled Monolayer on Au Substrate," Molecular Crystals and Liquid Crystals Science and Technology, vol. 370, (2001), pp. 277-283.

Naraokaa, R. et al., "Nonlinear Optical Property of Hemicyanine Self-Assembled Monolayers on Gold and its Absorption Kinetics Probed by Optical Second-Harmonic Generation and Surface Plasmon Resonance Spectroscopy," Chemical Physics Letters, vol. 362, No. 1-2, (2002), pp. 26-30.

Okawa, H. et al., "Synthesis and Characterization of an Alkanethiol Thin Film Containing a Hemicyanine Dye," Molecular Crystals and Liquid Crystals, vol. 377, (2002), pp. 137-140.

Tsuboi, K. et al., "Formation of Merocyanine Self-Assembled Monolayer and its Nonlinear Optical Properties Probed by Second-Harmonic Generation and Surface Plasmon Resonance," Japanese Journal of Applied Physics, vol. 42, No. 2A, (2003), pp. 607-613.

Wang, Y. et al., "Synthesis and Fluorescence Properties of Triad Compounds with Aromatic Sulfur Bridges," Dyes and Pigments, vol. 51, No. 2-3, (2001), pp. 127-136.

Wang, Y. et al., "Synthesis and Luminescence Properties of Triad Compounds with a Disulfide Bridge," vol. 54, No. 3, (2002), pp. 265-274.

Copending U.S. Appl. No. 12/233,955, filed Sep. 19, 2008.
Copending U.S. Appl. No. 12/234,001, filed Sep. 19, 2008.
Copending U.S. Appl. No. 12/234,072, filed Sep. 19, 2008.
Copending U.S. Appl. No. 12/234,135, filed Sep. 19, 2008.
Copending U.S. Appl. No. 12/282,586, filed Sep. 11, 2008.
English language Abstract of EP 2 001 960, dated Dec. 17, 2008.
English language Abstract of EP 2 004 757, dated Dec. 24, 2008.
English language Abstract of EP 2 018 847, dated Jan. 28, 2009.
English language Abstract of EP 2 062 945, dated May 27, 2009.
English language Abstract of WO 2007/110537, dated Oct. 4, 2007.
English language Abstract of WO 2007/110539, dated Oct. 4, 2007.
English language Abstract of WO 2007/110542, dated Oct. 4, 2007.
European Search Report for EP 08 16 4735, dated May 19, 2009.
French Search Report for FR 07/57753, dated Aug. 4, 2008.
French Search Report for FR 07/57755, dated Jul. 30, 2008.
French Search Report for FR 07/57773, dated Jul. 7, 2008.
French Search Report for FR 07/57778, dated Aug. 20, 2008.
Notice of Allowance mailed Jan. 11, 2010, in co-pending U.S. Appl. No. 12/233,955.
Notice of Allowance mailed Jan. 11, 2010, in co-pending U.S. Appl. No. 12/234,001.
Notice of Allowance mailed May 4, 2009, in co-pending U.S. Appl. No. 12/234,135.
Notice of Allowance mailed Nov. 6, 2009, in co-pending U.S. Appl. No. 12/234,072.
Notice of Allowance mailed Sep. 3, 2009, in co-pending U.S. Appl. No. 12/234,135.
Office Action mailed Apr. 28, 2009, in co-pending U.S. Appl. No. 12/234,072.
STIC Search Report for U.S. Appl. No. 12/233,955, dated Dec. 9, 2009.
STIC Search Report for U.S. Appl. No. 12/234,001, dated Dec. 7, 2009.
STIC Search Report for U.S. Appl. No. 12/234,072, dated Apr. 23, 2009.
STIC Search Report dated Apr. 27, 2009, for U.S. Appl. No. 12/234,135.
"Sulfide Hair Dyes", CIBA, IP.Com document IPCOM000130141D, Oct. 13, 2005.

* cited by examiner

FIGURE 1. Reflectance of locks treated with compound 1 at application and after 5 shampooing operations.
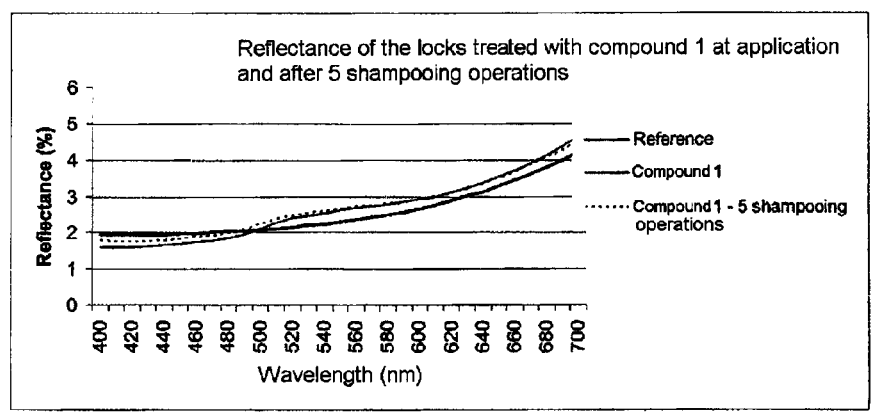

FLUORESCENT ENTITY, DYEING COMPOSITION CONTAINING AT LEAST ONE FLUORESCENT ENTITY, AND METHOD FOR LIGHTENING KERATIN MATERIALS USING SAID AT LEAST ONE FLUORESCENT ENTITY

CROSS REFERENCE TO RELATED APPLICATIONS

This application is a national phase application based on PCT/FR2007/050997, filed Mar. 23, 2007, which claims the priority of French Patent Application Nos. 0651035, filed Mar. 24, 2006, and 0753076, filed Feb. 5, 2007; and claims the benefit of U.S. Provisional Application Nos. 60/792,941, filed Apr. 19, 2006, and 60/901,324, filed Feb. 15, 2007, the contents of all of which are incorporated herein by reference.

The invention relates to the dyeing of keratin materials using naphthylimide thiol/disulphide fluorescent dyes.

It is known practice to dye keratin fibres, in particular human keratin fibres, by direct dyeing. The process conventionally used in direct dyeing comprises applying to the keratin fibres direct dyes which are coloured or colouring molecules having an affinity for the fibres, allowing them to diffuse and then rinsing the fibres.

The direct dyes which are conventionally used are, for example, dyes of the nitrobenzene type, anthroquinone dyes, nitropyridine dyes, or dyes of the azo, xanthene, acridine, azine or triarylmethane type.

The colourings which result from the use of direct dyes are temporary or semipermanent colourings since the nature of the interactions which bind the direct dyes to the keratin fibre and their disorption from the surface and/or from the core of the fibre are responsible for their weak dyeing power and for their poor resistance to washing operations or to perspiration.

Moreover, the colouring of keratin fibres using conventional direct dyes does not make it possible to significantly lighten keratin fibres.

The lightening of the colour of keratin fibres, more particularly dark keratin fibres to lighter shades, by optionally modifying the shade thereof, constitutes an important demand.

Conventionally, in order to obtain a lighter colouring, a chemical bleaching process is used. This process comprises treating the keratin materials, such as keratin fibres, in particular the hair, with a strong oxidizing system, generally composed of hydrogen peroxide, possibly in combination with persalts, generally in an alkaline medium.

This bleaching system has the drawback of damaging keratin materials, in particular keratin fibres, especially human keratin fibres such as the hair, and of detrimentally affecting their cosmetic properties. The fibres in fact have a tendency to become rough, more difficult to disentangle and more brittle. Finally, the lightening or bleaching of keratin fibres using oxidizing agents is incompatible with the treatments for modifying the shape of said fibres, particularly in hair straightening treatments.

Another lightening technique comprises applying fluorescent direct dyes to dark hair. This technique, described in particular in documents FR 2 830 189 and WO 2004/091473, makes it possible to retain the quality of the keratin fibre during the treatment, but the fluorescent dyes used do not exhibit satisfactory resistance to shampooing operations.

In order to increase the fastness of direct dyes, it is known practice to fix direct dyes by covalent bonding to the hair. For example, it is known practice to react dyes comprising reactive groups with the very numerous cystine or cysteine residues in keratin fibres; see, for example, *Journal of the Society of Dyers and Colourists*, Guise and Stapleton, 91, 259-264 (1975); *Journal of Cosmetic Chemistry*, 42, 1-17 (1991); CA 2024509.

Furthermore, it is known practice to protect the thiol function(s) contained in a molecule to be grafted to the hair before applying them to said hair, WO 99/51194.

Other disulphide dyes known for dyeing keratin fibres are disulphide derivatives of aminothiophenol derivatives. Such dyes are described, for example, in patent FR 1156407. These dyes can be used under relatively mild conditions, in the presence of a slightly reducing medium or after a reducing pre-treatment of the hair. However, these dyes can bring about colour changes during application.

Finally, document WO 2005/097051 describes azaimidazolium disulphide dyes for the direct dyeing of keratin fibres.

The aim of the present invention is to provide new systems for dyeing keratin materials, in particular human keratin fibres, especially the hair, which do not have the drawbacks of the existing bleaching processes. In particular, one of the aims of the present invention is to provide direct dyeing systems for obtaining lightening effects, especially on naturally or artificially dark keratin fibres, which are resistant to successive shampooing operations, which do not damage the keratin fibres and which do not detrimentally affect their cosmetic properties.

This aim is achieved with the present invention, a subject of which is a process for dyeing keratin materials, in particular keratin fibres, especially human keratin fibres such as the hair, more particularly dark hair, comprising applying, to the keratin materials, a dye composition comprising, in a cosmetically suitable medium, at least one thiol fluorescent dye, chosen from the dyes of formulae (I) to (VI) below:

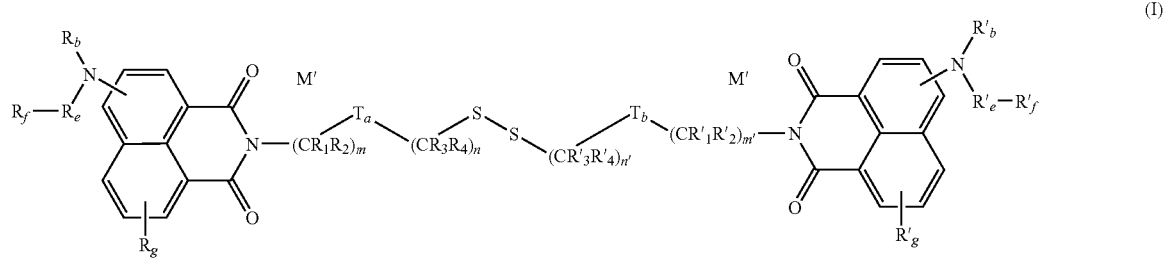

(I)

-continued

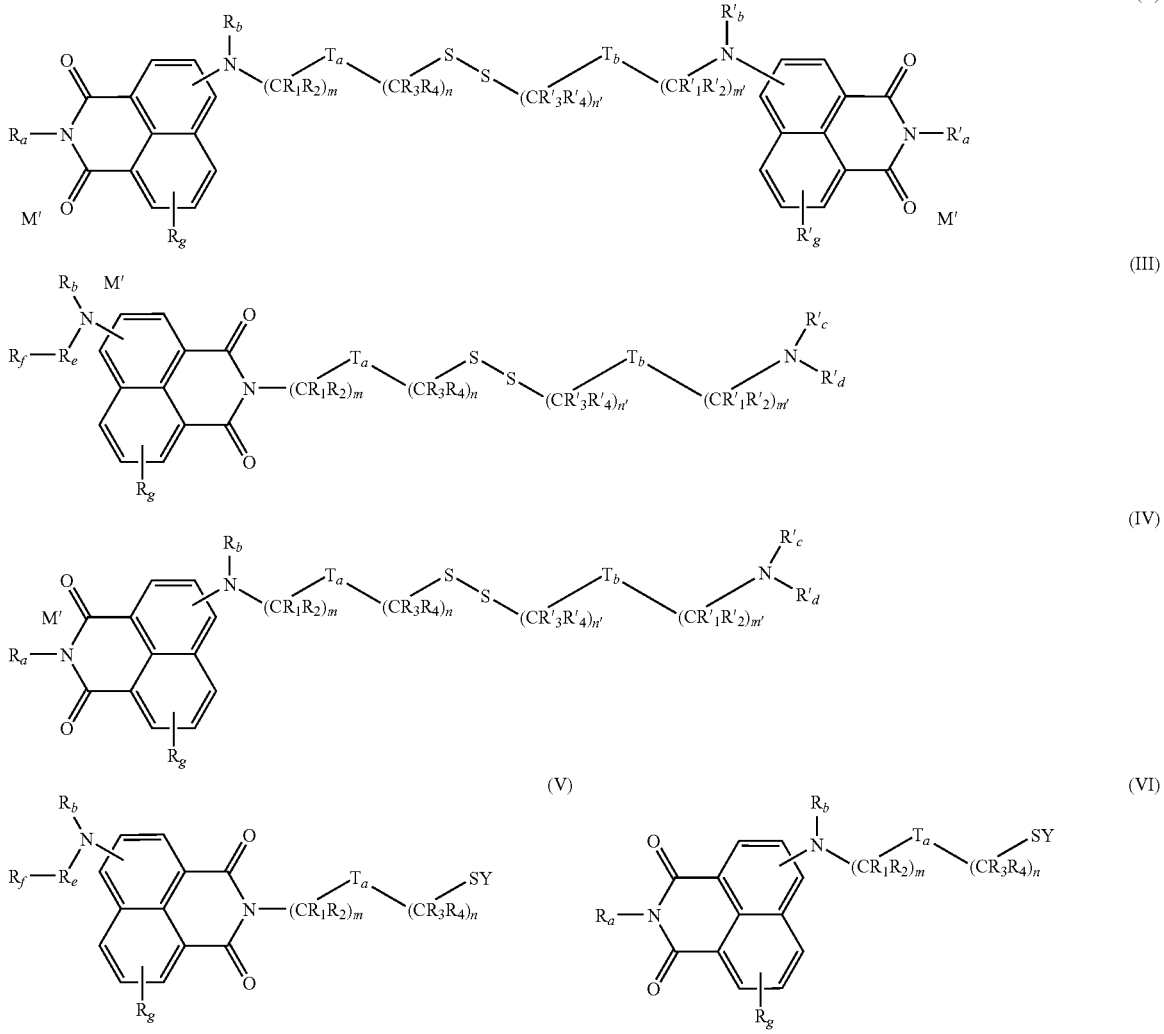

the organic or mineral acid salts, optical isomers and geometrical isomers thereof, and the solvates such as hydrates;

in which formulae (I) to (VI):

- $R_a$ and $R'_a$, which may be identical or different, represent an aryl($C_1$-$C_4$)alkyl group or a ($C_1$-$C_6$)alkyl group optionally substituted with a hydroxyl group or a di($C_1$-$C_4$)(alkyl)amino group, it being possible for said alkyl radicals to form, with the nitrogen atom which bears them, a heterocycle comprising from 5 to 7 members, optionally comprising another heteroatom which may or may not be different from nitrogen; preferably, $R_a$ and $R'_a$ represent a ($C_1$-$C_3$) alkyl group optionally substituted with a hydroxyl group, or a benzyl group;

- $R_b$ and $R'_b$, which may be identical or different, represent a hydrogen atom, an aryl($C_1$-$C_4$) alkyl group or a ($C_1$-$C_6$) alkyl group which is optionally substituted; in particular, $R_b$ and $R'_b$ represent a hydrogen atom or a ($C_1$-$C_3$)alkyl or benzyl group;

- $R'_c$ and $R'_d$, which may be identical or different, represent a hydrogen atom, an aryl($C_1$-$C_4$)alkyl group, or a $C_1$-$C_6$ alkyl group which is optionally substituted;

- $R_e$ and $R'_e$, which may be identical or different, represent an optionally unsaturated, linear or branched, divalent ($C_1$-$C_6$)alkylenyl hydrocarbon-based chain;

- $R_f$ and $R'_f$, which may be identical or different, represent i) a quaternary ammonium group (R")(R''')(R'''')N+—, M' where R", R''', and R'''' which may be identical or different, represent a hydrogen atom or a ($C_1$-$C_4$)alkyl group, or else (R")(R''')(R'''')N+ represents an optionally substituted cationic heteroaryl group, in particular an imidazolium group optionally substituted with a ($C_1$-$C_3$)alkyl group and M' represents an anionic counterion; ii) a hydroxyl group; iii) ($C_1$-$C_6$)(di)(alkyl)amino; or iv) an optionally substituted noncationic heteroaryl such as imidazolyl;

- $R_g$ and $R'_g$, which may be identical or different, represent a hydrogen or halogen atom, an amino, (di)($C_1$-$C_4$)alkylamino, cyano, carboxyl, hydroxyl, trifluoromethyl, acylamino, $C_1$-$C_4$ alkoxy, $C_2$-$C_4$ (poly)hydroxyalkoxy, ($C_1$-$C_4$)alkyl-carbonyloxy ($C_1$-$C_4$)alkoxycarbonyl, ($C_1$-$C_4$)alkyl-carbonylamino, acylamino, carbamoyl or ($C_1$-$C_4$)alkylsulphonylamino group, an aminosulphonyl radical, or a ($C_1$-$C_{16}$)alkyl radical optionally substituted with a group chosen from ($C_1$-$C_{12}$)alkoxy, hydroxyl, cyano, carboxyl, amino and (di)($C_1$-$C_4$)alkylamino, or else the two alkyl radicals borne by the nitrogen atom of the amino group form a heterocycle comprising from 5 to 7 members and optionally comprising another heteroatom identical to or different from that of the nitrogen atom; in particular, $R_g$ and $R'_g$ represent a hydrogen atom;

$R_1$, $R'_1$, $R_2$, $R'_2$, $R_3$, $R'_3$, $R_4$ and $R'_4$, which may be identical or different, represent a hydrogen atom or a ($C_1$-$C_4$) alkyl, ($C_1$-$C_4$)alkoxy, hydroxyl, cyano, carboxyl or (di) ($C_1$-$C_4$)(alkyl)amino group, it being possible for said alkyl radicals to form, with the nitrogen atom which bears them, a heterocycle comprising from 5 to 7 members, optionally comprising another heteroatom which may or may not be different from nitrogen; especially, $R_1$, $R'_1$, $R_2$, $R'_2$, $R_3$, $R'_3$, $R_4$ and $R'_4$ are hydrogen atoms or an amino group; in particular, $R_1$, $R'_1$, $R_2$, $R'_2$, $R_3$, $R'_3$, $R_4$ and $R'_4$ represent a hydrogen atom;

$T_a$ and $T_b$, which may be identical or different, represent:
i) either a σ covalent bond,
ii) or one or more radicals or combinations thereof chosen from —$SO_2$—, —O—, —S—, —N(R)—, —$N^+$(R)($R^o$)— and —C(O)—, with R and $R^o$, which may be identical or different, representing a hydrogen atom, a $C_1$-$C_4$ alkyl radical, a $C_1$-$C_4$ hydroxyalkyl radical or an aryl($C_1$-$C_4$)alkyl; in particular, $T_a$ and $T_b$ represent a σ covalent bond or a group chosen from —N(R)—, —C(O)—, —C(O)—N(R)—, —N(R)—C(O)—, —C(O)—N(R)—C(O)—, —O—C(O)—, —C(O)—O— and —$N^+$(R)($R^o$)—, with R and $R^o$, which may be identical or different, representing a hydrogen atom or a $C_1$-$C_4$ alkyl alkyl group; in particular, $T_a$ and $T_b$ represent a σ bond;
iii) or a preferably monocyclic, cationic or noncationic, heterocycloalkyl or heteroaryl radical containing especially two heteroatoms, in particular two nitrogen atoms, and comprising in particular from 5 to 7 members, such as imidazolium, piperidyl, homopiperidyl, piperidinium or homopiperidinium optionally substituted with a ($C_1$-$C_4$)alkyl group such as methyl;

m, m', n and n', which may be identical or different, represent an integer between 0 and 6 inclusive, with m+n and m'+n', which may be identical or different, representing an integer between 1 and 10 inclusive; in particular, the sum m+n=m'+n' is an integer between 4 and 6 inclusive; and Y represents: i) a hydrogen atom; ii) an alkali metal; iii) an alkaline earth metal; iv) an ammonium group: $N^+R^\alpha R^\beta R^\gamma R^\delta$ or a phosphonium group: $P^+R^\alpha R^\beta R^\gamma R^\delta$ with $R^\alpha$, $R^\beta$, $R^\gamma$ and $R^\delta$, which may be identical or different, representing a hydrogen atom or a ($C_1$-$C_4$)alkyl group; or v) a thiol-function-protecting group;

it being understood that when the compounds of formula (I) to (VI) contain one or more cationic parts, it is associated with one or more anionic counterions allowing formulae (I) to (VI) to achieve electroneutrality.

Another subject of the invention is a dye composition comprising, in a suitable cosmetic medium, at least one fluorescent dye of formula (I) to (VI) as defined above, and optionally a reducing agent.

A subject of the invention is also novel thiol fluorescent dyes of formula (I) to (VI) as defined above.

The dyeing process according to the invention makes it possible to visibly colour dark keratin materials, in particular dark human keratin fibres, especially dark hair.

Furthermore, the process of the invention makes it possible to obtain colouring of keratin materials, in particular human keratin fibres, especially the hair, without damaging said material, which is persistent with respect to shampooing operations, common attacks (sunlight, perspiration), and other hair treatments. The process of the invention also makes it possible to obtain lightening of keratin materials such as keratin fibres, in particular dark keratin fibres, and more particular dark hair.

For the purpose of the invention, the term "dark keratin material" is intended to mean that which exhibits a lightness of L* measured in the C.I.E.L. L*a*b* system of less than or equal to 45, and preferably less than or equal to 40, given that, moreover, L*=0 is equivalent to black and L*=100 is equivalent to white.

For the purpose of the invention, the expression "naturally or artificially dark hair" is intended to mean hair whose tone height is less than or equal to 6 (dark blonde) and preferably less than or equal to 4 (chestnut-brown).

The lightening of the hair is evaluated by the variation in "tone height" before or after application of the compound of formula (I) to (VI).

The notion of "tone" is based on the classification of the natural shades, one tone separating each shade from the shade immediately following or preceding it. This definition and the classification of the natural shades are well known to hair styling professionals and are published in the book "Science des traitement capillaires" [Hair treatment sciences], by Charles Zviak 1988, published by Masson, pp. 215 and 278.

The tone heights range from 1 (black) to 10 (very light blonde), one unit corresponding to one tone; the higher the figure, the lighter the shade.

An artificially coloured hair is a hair whose colour has been modified by a dyeing treatment, for example dyeing with direct dyes or oxidation dyes.

Preferably, the composition should, after application to hair, for example chestnut-brown hair, lead to the results below.

Interest is focussed on the reflectance performance levels of the hair when it is irradiated with visible light in the wavelength range from 400 to 700 nanometers.

The curves of reflectance as a function of wavelength, of hair treated with the composition of the invention and of untreated hair, are then compared.

The curve corresponding to the treated hair should show a reflectance in the wavelength range of from 450 to 700 nanometers which is higher than the curve corresponding to the untreated hair.

This means that, in the wavelength range from 450 to 700 nanometers, there is at least one range where the reflectance curve corresponding to the treated hair is higher than the reflectance curve corresponding to the untreated hair. The term "higher" is intended to mean a difference of at least 0.05% in reflectance, preferably of at least 0.1%. All the same, there may be, in the wavelength range of from 450 to 700 nanometers, at least one range where the reflectance curve corresponding to the treated hair is superimposable or lower than the reflectance curve corresponding to the untreated hair.

Preferably, the wavelength where the difference is at a maximum between the reflectance curve of the treated hair and that of the untreated hair is within the wavelength range of from 450 to 650 nanometers, and preferably within the wavelength range of from 450 to 620 nanometers.

For the purpose of the present invention, and unless otherwise indicated:

the "aryl" or "heteroaryl" radicals or the aryl or heteroaryl part of a radical may be substituted with at least one substituent borne by a carbon atom, chosen from:

- a $C_1$-$C_{16}$, preferably $C_1$-$C_8$, alkyl radical optionally substituted with one or more radicals chosen from the radicals: hydroxyl, $C_1$-$C_2$ alkoxy, $C_2$-$C_4$ (poly)hydroxyalkoxy, acylamino and amino substituted with two $C_1$-$C_4$ alkyl radicals, which may be identical or different, optionally bearing at least one hydroxyl group, or the two radicals possibly forming, with the nitrogen atom to which they are attached, a heterocycle comprising from 5 to 7 members, preferably 5 or 6 members, which is saturated or unsaturated, which is optionally substituted, and which optionally comprises another heteroatom which may be identical or different from the nitrogen;
- a halogen atom such as chlorine, fluorine or bromine;
- a hydroxyl group;
- a $C_1$-$C_2$ alkoxy radical;
- $C_1$-$C_2$ alkylthio radical;
- a $C_2$-$C_4$ (poly)hydroxyalkoxy radical;
- an amino radical;
- a 5- or 6-membered heterocycloalkyl radical;
- an optionally cationic 5- or 6-membered heteroaryl radical, preferably imidazolium, optionally substituted with a $C_1$-$C_4$ alkyl radical, preferably methyl;
- an amino radical substituted with one or two $C_1$-$C_6$ alkyl radicals, which may be identical or different, optionally bearing at least:
  i) one hydroxyl group,
  ii) one amino group optionally substituted with one or two optionally substituted $C_1$-$C_3$ alkyl radicals, said alkyl radicals possibly forming, with the nitrogen atom to which they are attached, a heterocycle comprising from 5 to 7 members, which is saturated or unsaturated, which is optionally substituted, and which optionally comprises at least one heteroatom which may or may not be different from nitrogen,
- —NR—COR' in which the R radical is a hydrogen atom or a $C_1$-$C_4$ alkyl radical optionally bearing at least one hydroxyl group, and the R' radical is a $C_1$-$C_2$ alkyl radical;
- $(R)_2N$—CO— in which the R radicals, which may or may not be identical, represent a hydrogen atom, or a $C_1$-$C_4$ alkyl radical optionally bearing at least one hydroxyl group;
- $R'SO_2$—NR— in which the R radical represents a hydrogen atom or a $C_1$-$C_4$ alkyl radical optionally bearing at least one hydroxyl group, and the R' radical represents a $C_1$-$C_4$ alkyl radical or a phenyl radical;
- $(R)_2N$—$SO_2$— in which the R radicals, which may or may not be identical, represent a hydrogen atom or a $C_1$-$C_4$ alkyl radical optionally bearing at least one hydroxyl group,
- a carboxylic radical in acid or salified form (preferably with an alkali metal or an ammonium, which is substituted or unsubstituted);
- a cyano group;
- a polyhaloalkyl group containing from 1 to 6 carbon atoms and from 1 to 6 halogen atoms, which may be identical or different; the polyhaloalkyl group is, for example, trifluoromethyl;

the cyclic or heterocyclic part of a nonaromatic radical may be substituted with at least one substituent borne by a carbon atom, chosen from the groups:

- hydroxyl;
- $C_1$-$C_4$ alkoxy;
- $C_2$-$C_4$ (poly)hydroxyalkoxy;
- a $C_1$-$C_2$ alkylthio radical;
- RCO—NR'— in which the R' radical is a hydrogen atom or a $C_1$-$C_4$ alkyl radical optionally bearing at least one hydroxyl group, and the R radical is a $C_1$-$C_2$ alkyl radical or an amino radical substituted with two $C_1$-$C_4$ alkyl groups, which may be identical or different, optionally bearing at least one hydroxyl group;
- RCO—O— in which the R radical is a $C_1$-$C_4$ alkyl radical or an amino radical substituted with one or two $C_1$-$C_4$ alkyl groups, which may be identical or different, optionally bearing at least one hydroxyl group, said alkyl radicals possibly forming, with the nitrogen atom to which they are attached, a heterocycle comprising from 5 to 7 members, which is saturated or unsaturated, which is optionally substituted, and which optionally comprises at least one other heteroatom which may or may not be different from nitrogen;
- RO—CO— in which the R radical is a $C_1$-$C_4$ alkyl radical optionally bearing at least one hydroxyl group;
- a cyclic or heterocyclic radical or a nonaromatic part of an aryl or heteroaryl radical may also be substituted with one or more oxo or thioxo groups;
- an "aryl" radical represents a condensed or noncondensed, monocyclic or polycyclic group containing from 6 to 22 carbon atoms, and at least one ring of which is aromatic; preferably, the aryl radical is a phenyl, biphenyl, naphthyl, indenyl, anthracenyl or tetrahydronaphthyl;
- a "diarylalkyl" radical represents a group comprising, on the same carbon atom of an alkyl group, two aryl groups, which may be identical or different, such as diphenylmethyl or 1,1-diphenylethyl;
- a "heteroaryl radical" represents an optionally cationic, condensed or noncondensed, monocyclic or polycyclic group comprising from 5 to 22 members and from 1 to 6 heteroatoms chosen from a nitrogen, oxygen, sulphur and selenium atom, and at least one ring of which is aromatic; preferably, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenooxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl and its ammonium salt;
- a "diheteroarylalkyl" radical represents a group comprising, on the same carbon atom of an alkyl group, two heteroaryl groups, which may be identical or different, such as difurylmethyl, 1,1-difurylethyl, dipyrrolylmethyl or dithienylmethyl;
- a "cyclic radical" is a condensed or noncondensed, monocyclic or polycyclic, nonaromatic cycloalkyl radical containing from 5 to 22 carbon atoms, possibly comprising one or more unsaturations; in particular, the cyclic radical is a cyclohexyl;
- a "sterically hindered cyclic" radical is a substituted or unsubstituted, aromatic or nonaromatic, cyclic radical hindered by steric effect or constraint, comprising from 6 to 14 members, which may be bridged; by way of sterically hindered radicals, mention may be made of bicyclo[1.1.0]butane, mesityls such as 1,3,5-trimethylphenyl, 1,3,5-tri-tert-butylphenyl, 1,3,5-isobutylphenyl, 1,3,5-trimethylsilylphenyl and adamantyl;

a "heterocyclic radical or heterocycle" is a condensed or noncondensed, monocyclic or polycyclic, nonaromatic radical containing from 5 to 22 members, comprising from 1 to 6 heteroatoms chosen from nitrogen, oxygen, sulphur and selenium;

an "alkyl radical" is a linear or branched, $C_1$-$C_{16}$, preferably $C_1$-$C_8$, hydrocarbon-based radical;

the expression "optionally substituted" assigned to the alkyl radical implies that said alkyl radical may be substituted with one or more radicals chosen from the radicals: i) hydroxyl; ii) $C_1$-$C_4$ alkoxy; iii) acylamino; iv) amino optionally substituted with one or two $C_1$-$C_4$ alkyl radicals, which may be identical or different, said alkyl radicals possibly forming, with the nitrogen atom which bears them, a heterocycle comprising from 5 to 7 members, optionally comprising another heteroatom which may or may not be different from nitrogen; v) or a quaternary ammonium group —$N^+R'R''R'''$, $M^-$ for which R', R'', R''', which may be identical or different, represent a hydrogen atom or a $C_1$-$C_4$ alkyl group, or else —$N^+R'R''R'''$ forms a heteroaryl such as imidazolium optionally substituted with a $C_1$-$C_4$ alkyl group, and $M^-$ represents the counterion of the corresponding organic acid, mineral acid or halide;

an "alkoxy radical" is an alkyloxy or alkyl-O-radical for which the alkyl radical is a linear or branched, $C_1$-$C_{16}$, preferably $C_1$-$C_8$, hydrocarbon-based radical;

an "alkylthio radical" is an alkyl-S— radical for which the alkyl radical is a linear or branched, $C_1$-$C_{16}$, preferably $C_1$-$C_8$, hydrocarbon-based radical; when the alkylthio group is optionally substituted, this implies that the alkyl group is optionally substituted as defined above;

the limits delimiting the extent of the range of values are included in this range of values;

an "organic or mineral acid salt" is more particularly chosen from a salt derived: i) from hydrochloric acid HCl; ii) from hydrobromic acid HBr; iii) from sulphuric acid $H_2SO_4$; iv) from alkylsulphonic acids: Alk-$S(O)_2OH$ such as methylsulphonic acid and ethylsulphonic acid; v) from arylsulphonic acids: Ar—$S(O)_2OH$ such as from benzenesulphonic acid and from toluenesulphonic acid; vi) from citric acid; vii) from succinic acid; viii) from tartaric acid; ix) from lactic acid; x) from alkoxysulphinic acids: Alk-O—S(O)OH such as from methoxysulphinic acid and from ethoxysulphinic acid; xi) from aryloxysulphinic acids such as from tolueneoxysulphinic acid and from phenoxysulphinic acid; xii) from phosphoric acid $H_3PO_4$; xiii) from acetic acid $CH_3COOH$; xiv) from triflic acid $CF_3SO_3H$ and xv) from tetrafluoroboric acid $HBF_4$;

an "anionic counterion" is an anion or an anionic group associated with the cationic charge of the dye; more particularly, the anionic counterion is chosen from: i) halides such as chloride or bromide; ii) nitrates; iii) sulphonates, among which are $C_1$-$C_6$ alkyl sulphonates: Alk-$S(O)_2O^-$ such as methyl sulphonate or mesylate and ethyl sulphonate; iv) aryl sulphonates: Ar—$S(O)_2O^-$ such as benzene sulphonate and toluenesulphonate or tosylate; v) citrate; vi) succinate; vii) tartrate; viii) lactate; ix) alkyl sulphites: Alk-O—S(O)$O^-$ such as methyl sulphite and ethyl sulphite; x) arylsulphites: Ar—O—S(O)$O^-$ such as benzenesulphite and toluenesulphite; xi) alkyl sulphates: Alk-O—S(O)$O^-$ such as methyl sulphate and ethyl sulphate; xii) aryl sulphates: Ar—O—S(O)$_2O^-$; xiii) phosphate; xiv) acetate; xv) triflate; and xvi) borates such as tetrafluoroborate.

The fluorescent dyes of formulae (I) to (VI) are compounds capable of absorbing in the UV radiation or visible range at a wavelength $\lambda_{abs}$ of between 250 and 800 nm and capable of re-emitting in the visible range at an emission wavelength $\lambda_{em}$ of between 400 and 700 nm.

Preferably, the fluorescent compounds of the invention are dyes capable of absorbing in the visible range $\lambda_{abs}$ of between 400 and 700 nm and of re-emitting in the visible range $\lambda_{em}$ of between 400 and 700 nm. More preferably, the fluorescent dyes of formulae (I) to (VI) are dyes capable of absorbing at a $\lambda_{abs}$ of between 400 nm and 550 nm and of re-emitting in the visible range at a $\lambda_{em}$ of between 450 and 620 nm.

The fluorescent compounds of formula (V) or (VI) of the invention contain an SY function which may be in the covalent form —S—Y or ionic form —$S^-Y^+$ depending on the nature of Y and on the pH of the medium.

A specific embodiment relates to the fluorescent dyes of formula (V) or (VI) comprising an SY function where Y represents a hydrogen atom or an alkali metal. Advantageously, Y represents a hydrogen atom.

In accordance with another specific embodiment of the invention, in the abovementioned formula (V) or (VI), Y is a protecting group known to those skilled in the art, for instance those described in the books "*Protective Groups in Organic Synthesis*", T. W. Greene, John Willey & Sons publisher, NY, 1981, pp. 193-217; *"Protecting Groups"*; P. Kocienski, Thieme, 3rd ed., 2005, chap. 5.

Particularly when, in formula (V) or (VI), Y represents a thiol-function-protecting group, Y is chosen from the following radicals:

($C_1$-$C_4$) alkylcarbonyl;
($C_1$-$C_4$) alkylthiocarbonyl;
($C_1$-$C_4$) alkoxycarbonyl;
($C_1$-$C_4$)alkoxythiocarbonyl;
($C_1$-$C_4$) alkylthiothiocarbonyl;
(di)($C_1$-$C_4$)(alkyl)aminocarbonyl;
(di)($C_1$-$C_4$)(alkyl)aminothiocarbonyl;
arylcarbonyl such as phenylcarbonyl;
aryloxycarbonyl;
aryl($C_1$-$C_4$) alkoxycarbonyl;
(di)($C_1$-$C_4$)(alkyl)aminocarbonyl such as dimethylaminocarbonyl;
($C_1$-$C_4$)(alkyl) arylaminocarbonyl;
carboxyl;
$SO_3^-$; $M^+$ with $M^+$ representing an alkali metal such as sodium or potassium;
optionally substituted aryl such as phenyl, dibenzosuberyl or 1,3,5-cycloheptatrienyl,
optionally substituted heteroaryl; including in particular the cationic or noncationic heteroaryl comprising from 1 to 4 heteroatoms below:
i) monocyclic comprising 5, 6 or 7 members, such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl, imidazolium;

ii) bicyclic comprising 8 to 11 members, such as indolyl, indolinium, benzoimidazolyl, benzoimidazolium, benzoxazolyl, benzoxazolium, dihydrobenzoxazolinyl, benzothiazolyl, benzothiazolium, pyridoimidazolyl, pyridoimidazolium, thienocycloheptadienyl, these monocyclic or bicyclic groups being optionally substituted with one or more groups such as ($C_1$-$C_4$) alkyl, for instance methyl, or polyhalo($C_1$-$C_4$)alkyl, for instance trifluoromethyl;

iii) or tricyclic ABC below:

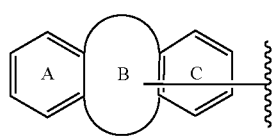

in which the two rings A, C optionally comprise a heteroatom, and the ring B is a 5-, 6- or 7-membered, particularly 6-membered ring and contains at least one heteroatom, for instance piperidyl or pyranyl;

optionally cationic, optionally substituted heterocycloalkyl, the heterocycloalkyl group represents in particular a saturated or partially saturated, 5-, 6- or 7-membered monocyclic group comprising from 1 to 4 heteroatoms chosen from oxygen, sulphur and nitrogen, such as di/tetrahydrofuranyl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidinyl, morpholinyl, di/tetra/hexahydroazepinyl or di/tetrahydropyrimidinyl, these groups being optionally substituted with one or more groups such as ($C_1$-$C_4$) alkyl, oxo or thioxo; or the heterocycle represents the following group:

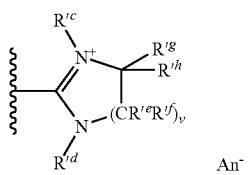

in which $R'^c$, $R'^d$, $R'^e$, $R'_f$, $R'^g$ and $R'^h$, which may be identical or different, represent a hydrogen atom or a ($C_1$-$C_4$) alkyl group, or else two groups $R'^g$ with $R'^h$, and/or $R'^e$ with $R'^f$, form an oxo or thioxo group, or else $R'^g$ with $R'^e$ together form a cycloalkyl; and v represents an integer between 1 and 3 inclusive; preferably, $R'^c$ to $R'^h$ represent a hydrogen atom; and An⁻ represents a counterion;

isothiouronium —C(NR'^cR'^d)=N⁺R'^eR'^f; An⁻ with $R'^c$, $R'^d$, $R'^e$ and $R'_f$ which may be identical or different, represent a hydrogen atom or a ($C_1$-$C_4$)alkyl group; preferably, $R'_c$ to $R'^f$ represent a hydrogen atom; and An⁻ represents a counterion;

isothiourea —C(NR'^cR'^d)=NR'^e; with $R'^c$, $R'^d$, $R'^e$ as defined above;

optionally substituted (di)aryl($C_1$-$C_4$)alkyl, such as 9-anthracenylmethyl, phenylmethyl or diphenylmethyl optionally substituted with one or more groups in particular chosen from ($C_1$-$C_4$) alkyl, ($C_1$-$C_4$) alkoxy such as methoxy, hydroxyl, ($C_1$-$C_4$)alkylcarbonyl and (di)($C_1$-$C_4$)(alkyl)amino such as dimethylamino;

optionally substituted (di)heteroaryl($C_1$-$C_4$)alkyl, the heteroaryl group is in particular cationic or noncationic, and monocyclic, comprising 5 or 6 members and from 1 to 4 heteroatoms chosen from nitrogen, oxygen and sulphur, such as the groups pyrrolyl, furanyl, thiophenyl, pyridyl, pyridyl N-oxide such as 4-pyridyl or 2-pyridyl N-oxide, pyrylium, pyridinium or triazinyl, optionally substituted with one or more groups such as alkyl, particularly methyl, advantageously the (di)heteroaryl($C_1$-$C_4$)alkyl is (di)heteroarylmethyl or (di)heteroarylethyl;

$CR^1R^2R^3$ with $R^1$, $R^2$ and $R^3$, which may be identical or different, representing a halogen atom or a group chosen from:
($C_1$-$C_4$) alkyl;
($C_1$-$C_4$) alkoxy;
optionally substituted aryl, such as phenyl optionally substituted with one or more groups such as ($C_1$-$C_4$) alkyl, ($C_1$-$C_4$)alkoxy or hydroxyl;
optionally substituted heteroaryl, such as thiophenyl, furanyl, pyrrolyl, pyranyl or pyridyl, optionally substituted with a ($C_1$-$C_4$)alkyl group;
$P(Z^1)R'^{i1}R'^{i2}R'^{i3}$ with $R'^{i1}$ and $R'^{i2}$, which may be identical or different, representing a hydroxyl, ($C_1$-$C_4$)alkoxy or alkyl group, $R'^{i3}$ representing a hydroxyl or ($C_1$-$C_4$) alkoxy group and $Z^1$ representing an oxygen or sulphur atom;
a sterically hindered cyclic group such as the adamantyl group; and
optionally substituted alkoxy($C_1$-$C_4$)alkyl, such as methoxymethyl (MOM), ethoxyethyl (EOM) or isobutoxymethyl.

According to a specific embodiment, the protected thiol fluorescent dyes of formula (V) or (VI) comprising a group Y i) which is a cationic, aromatic 5- or 6-membered monocyclic heteroaryl group comprising from 1 to 4 heteroatoms chosen from oxygen, sulphur and nitrogen, such as oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinyl, pyrazinium, pyridazinium, triazinium, tetrazinium, oxazepinium, thiepinyl, thiepinium or imidazolium; ii) cationic 8- to 11-membered bicyclic heteroaryl group, such as indolinium, benzoimidazolium, benzoxazolium or benzothiazolium, these monocyclic or bicyclic heteroaryl groups being optionally substituted with one or more groups such as alkyl, for instance methyl, or polyhalo($C_1$-$C_4$)alkyl, for instance trifluoromethyl; iii) or heterocyclic group below:

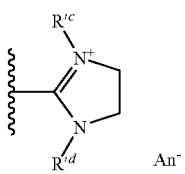

in which $R'^c$ and $R'^d$, which may be identical or different, represent a hydrogen atom or a ($C_1$-$C_4$)alkyl group; preferably, $R'^c$ to $R'^d$ represent a ($C_1$-$C_4$)alkyl group such as methyl; and An⁻ represents a counterion.

In particular, Y represents a group chosen from oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinium, pyridazinium, triazinium, imidazolium, benzoimidazolium, benzoxazolium and benzothiazolium, these groups being optionally substituted with one or more ($C_1$-$C_4$) alkyl groups, in particular methyl.

In particular, Y represents an alkali metal or a protecting group such as:
- ($C_1$-$C_4$)alkylcarbonyl, such as methylcarbonyl or ethylcarbonyl;
- arylcarbonyl such as phenylcarbonyl;
- ($C_1$-$C_4$) alkoxycarbonyl;
- aryloxycarbonyl;
- aryl($C_1$-$C_4$) alkoxycarbonyl;
- (di)($C_1$-$C_4$)(alkyl)aminocarbonyl such as dimethylaminocarbonyl;
- ($C_1$-$C_4$)(alkyl) arylaminocarbonyl;
- optionally substituted aryl, such as phenyl;
- 5- or 6-membered monocyclic heteroaryl, such as imidazolyl or pyridyl;
- 5- or 6-membered cationic monocyclic heteroaryl, such as pyrylium, pyridinium, pyrimidinium, pyrazinium, pyridazinium, triazinium or imidazolium; these groups being optionally substituted with one or more identical or different ($C_1$-$C_4$)alkyl groups, such as methyl;
- 8- to 11-membered cationic bicyclic heteroaryl, such as benzoimidazolium or benzoxazolium; these groups being optionally substituted with one or more identical or different ($C_1$-$C_4$)alkyl groups, such as methyl;
- cationic heterocycle of formula below:

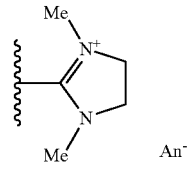

- isothiouronium —$C(NH_2)=N^+H_2$; $An^-$,
- isothiourea —$C(NH_2)=NH$;
- $SO_3^-$, $M^+$ with $M^+$ representing an alkali metal such as sodium or potassium.

By way of example of fluorescent dyes, mention may in particular be made of the following compounds:

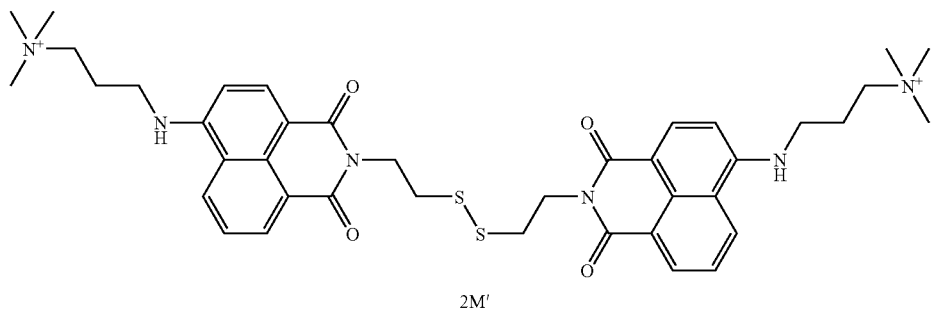

1

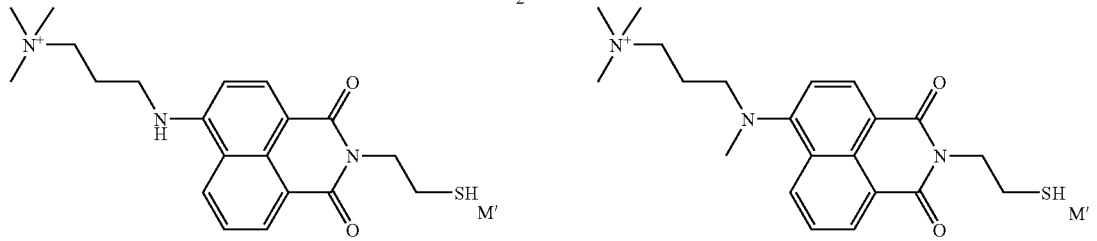

2

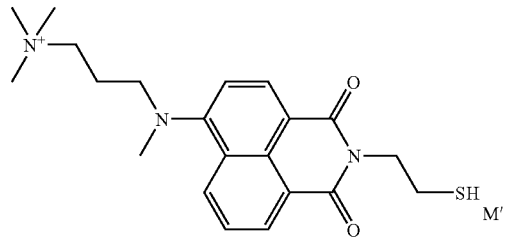

3

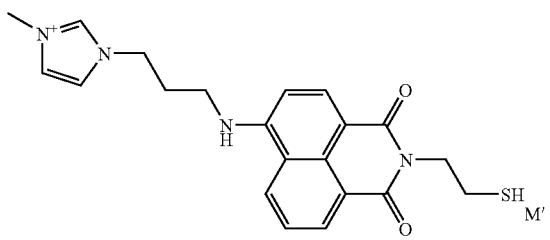

4

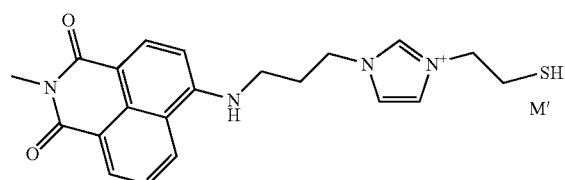

5

-continued
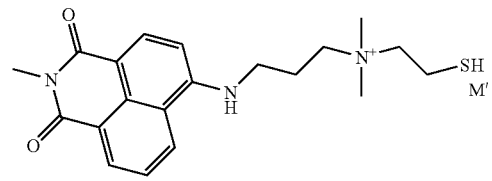
5
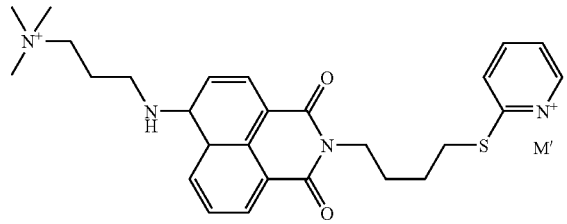
7
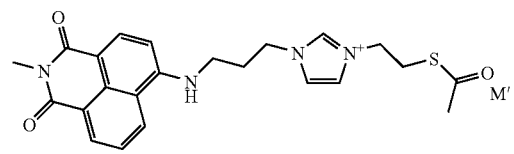
8
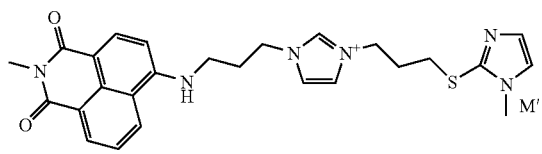
9
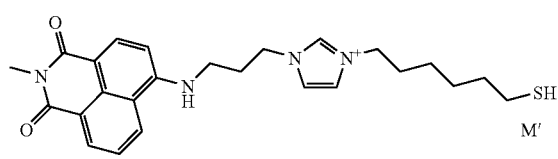
10
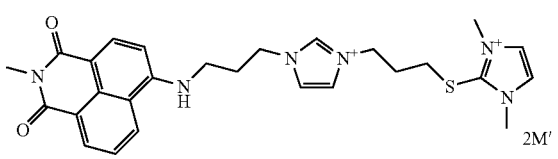
11
12
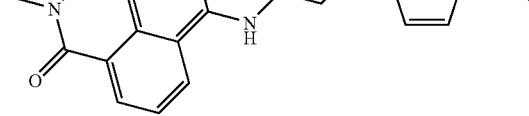
13
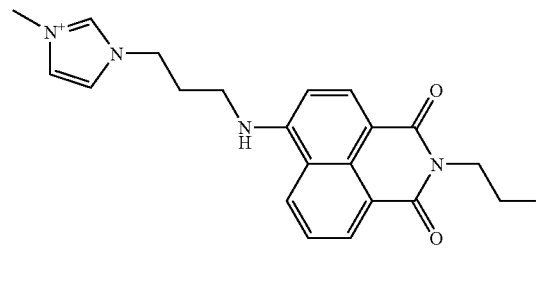
14
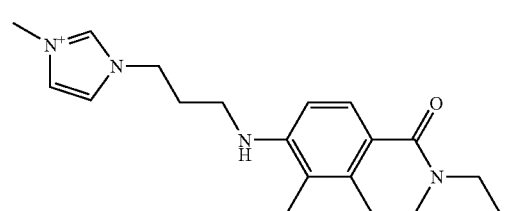
15

-continued
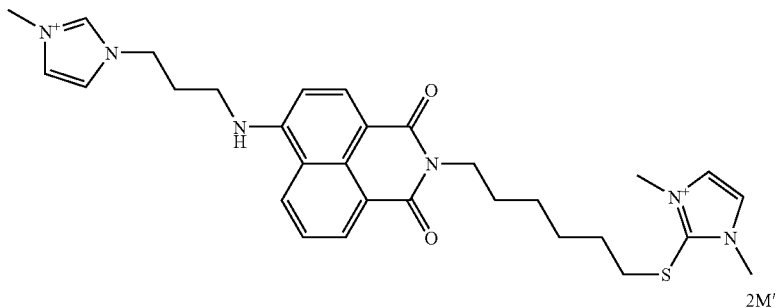
16
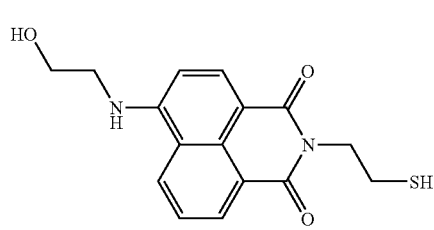
17
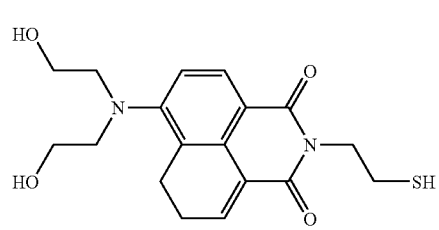
18
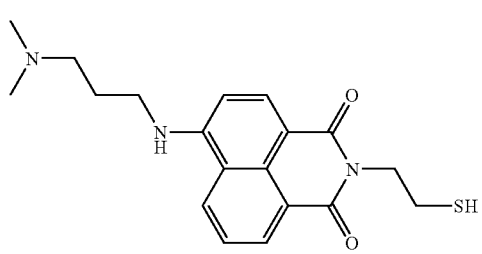
19
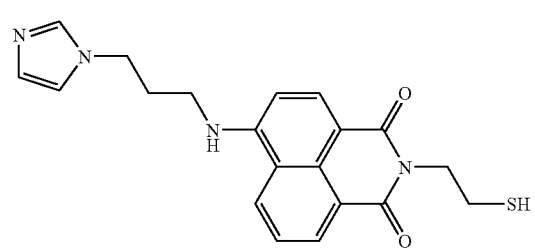
20
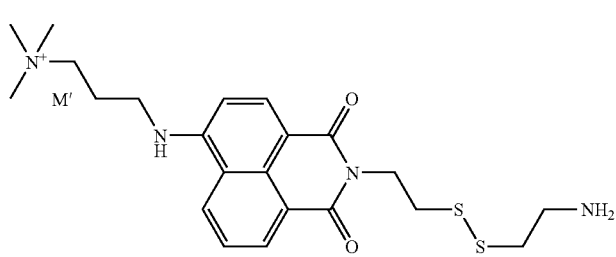
21
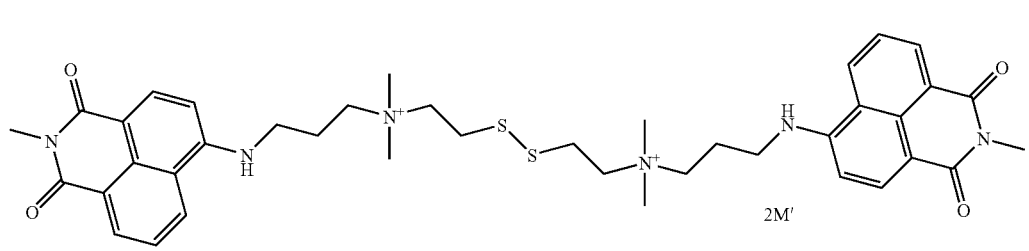
22
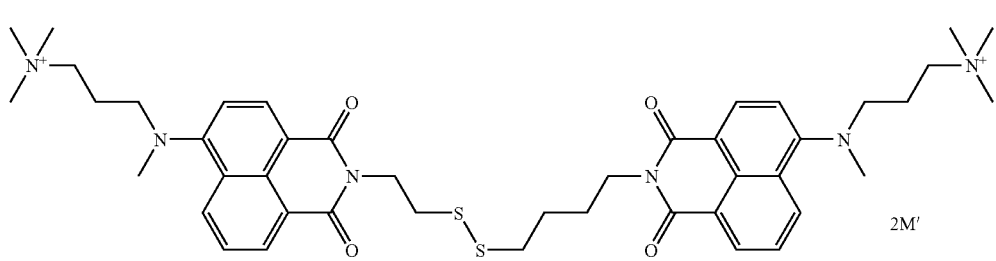
23

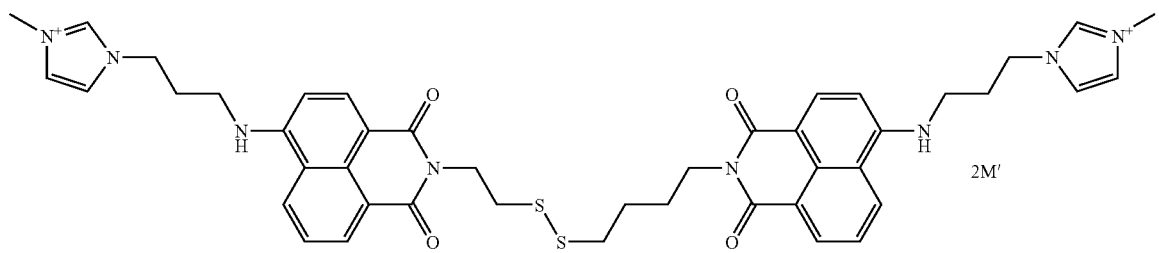

24

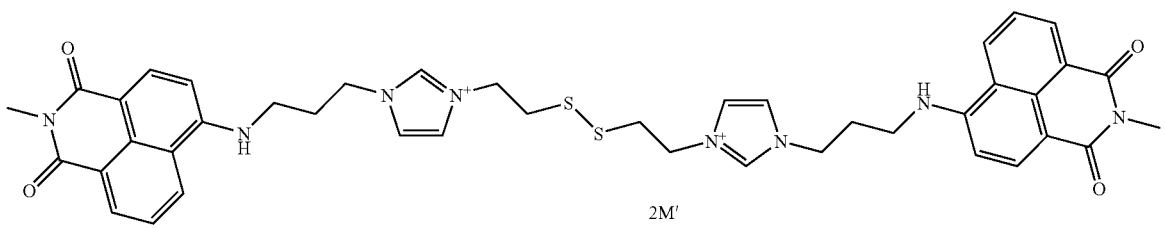

25 with M', which may be identical or different, representing an anionic counterion.

The protected thiol dyes of formulae (V') and (V") can be synthesized in two stages. The first stage consists in preparing the nonprotected thiol dye (a) according to the methods known to those skilled in the art, for instance "*Thiols and organic Sulfides*", "*Thiocyanates and Isothiocyanates, organic*", Ullmann's Encyclopaedia, Wiley-VCH, Weinheim, 2005. In addition, the second stage consists in protecting the thiol function according to the conventional methods known to those skilled in the art for producing protected thiol dyes of formulae (V') and (V"). By way of example for protecting the thiol function —SH of the thiol dye, use may be made of the methods in the books "*Protective Groups in Organic Synthesis*", T. W. Greene, John Willey & Sons ed., NY, 1981, pp. 193-217; "*Protecting Groups*", P. Kocienski, Thieme, 3rd ed., 2005, chap. 5.

This method can be illustrated by means of the method consisting i) in generating thiol fluorescent dyes of formula (a) by reduction of a naphthylimide two-chromophore fluorescent dye bearing a disulphide function —S—S— such as (Ia) and ii) in protecting, according to the conventional methods, said thiol function of (a) with the reactant (b)Y'R in order to obtain the protected thiol fluorescent dyes of formula (V'). The thiol compound (a) can also be metallated with an alkali metal or alkaline earth metal Met* so as to produce the thiolate fluorescent dye of formula (V").

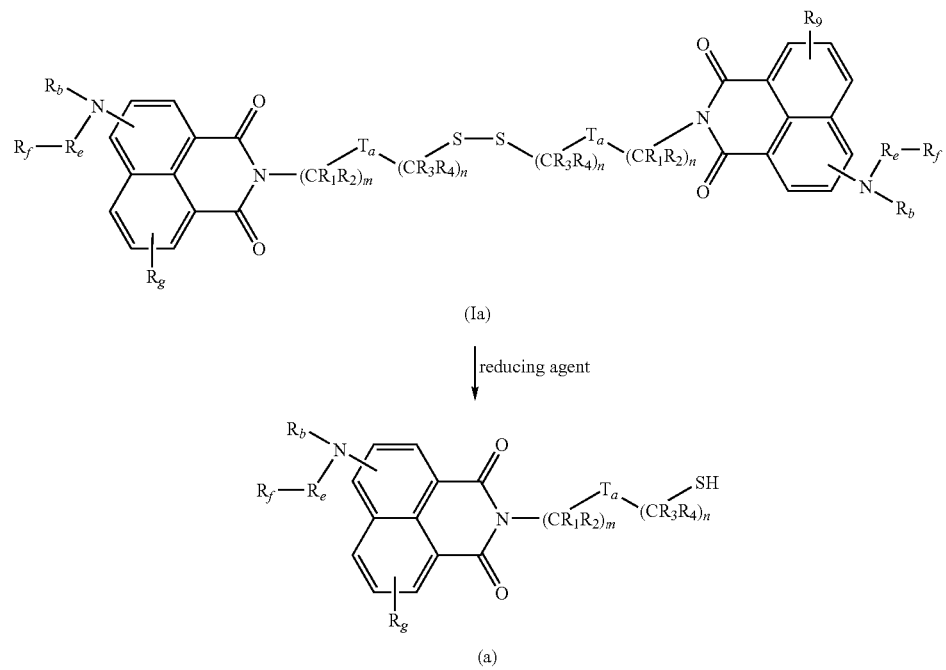

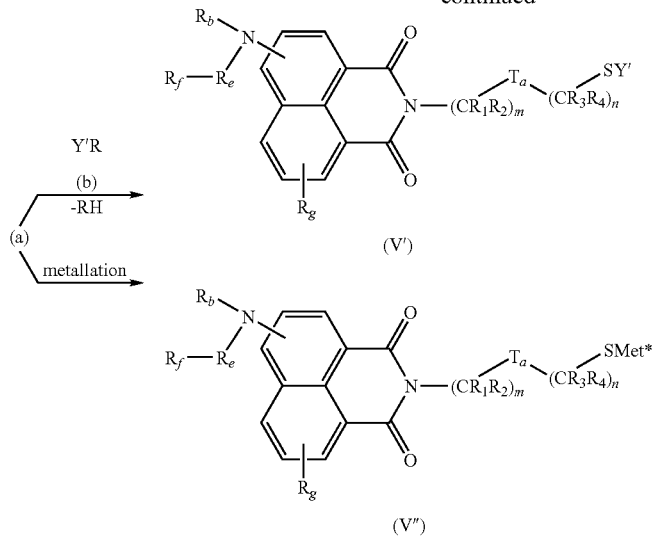

Another alternative for synthesizing a thiol dye comprising a naphthylimide unit is to condense, with the reactant comprising the naphthylimide group (c), a reactant bearing the thiol group protected by Y', such as the reactant (d):

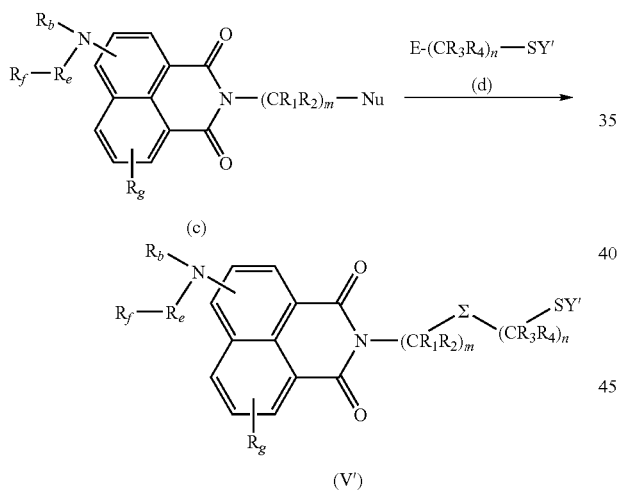

By way of example, the Σ covalent bonds that can be generated are listed in the table below, based on condensation of electrophiles with nucleophiles:

| Electrophiles E | Nucleophiles Nu | Σ covalent bonds |
| --- | --- | --- |
| Activated esters* | Amines | Carboxamides |
| Acyl azides** | Amines | Carboxamides |
| Acyl halides | Amines | Carboxamides |
| Acyl halides | Alcohols | Esters |
| Acyl cyanides | Alcohols | Esters |
| Acyl cyanides | Amines | Carboxamides |
| Alkyl halides | Amines | Alkylamines |
| Alkyl halides | Carboxylic acids | Esters |
| Alkyl halides | Thiols | Thioesters |
| Alkyl halides | Alcohols | Ethers |

-continued

| Electrophiles E | Nucleophiles Nu | Σ covalent bonds |
| --- | --- | --- |
| Sulphonic acids and esters thereof | Thiols | Thioethers |
| Sulphonic acids and esters thereof | Carboxylic acids | Esters |
| Sulphonic acids and esters thereof | Alcohols | Ethers |
| Anhydrides | Alcohols | Esters |
| Anhydrides | Amines | Carboxamides |
| Aryl halides | Thiols | Thioethers |
| Aryl halides | Amines | Arylamines |
| Aziridines | Thiols | Thioethers |
| Carboxylic acids | Amines | Carboxamides |
| Carboxylic acids | Alcohols | Esters |
| Carbodiimides | Carboxylic acids | N-arylurea or anhydrides |
| Diazoalkanes | Carboxylic acids | Esters |
| Epoxides | Thiols | Thioethers |
| Haloacetamides | Thiols | Thioethers |
| Imide esters | Amines | Amidines |
| Isocyanates | Amines | Ureas |
| Isocyanates | Alcohols | Urethanes |
| Isothiocyanates | Amines | Thioureas |
| Maleimides | Thiols | Thioethers |
| Sulphonic esters | Amines | Alkylamines |
| Sulphonic esters | Thiols | Thioethers |
| Sulphonic esters | Carboxylic acids | Esters |
| Sulphonic esters | Alcohols | Ethers |
| Sulphonyl halides | Amines | Sulphonamides |

*the activated esters of general formula —CO-Part with Part representing a leaving group such as oxysuccinimidyl, oxybenzotriazolyl, aryloxy which is optionally substituted;
**the acyl azides can be rearranged to give isocyanates.

The possible synthesis pathways can be illustrated by means of the synthesis of examples (g), (k) and (m) belonging to general formula (V) using the reactants (e) and (f), (h) and (j), (h') and (HSY'):

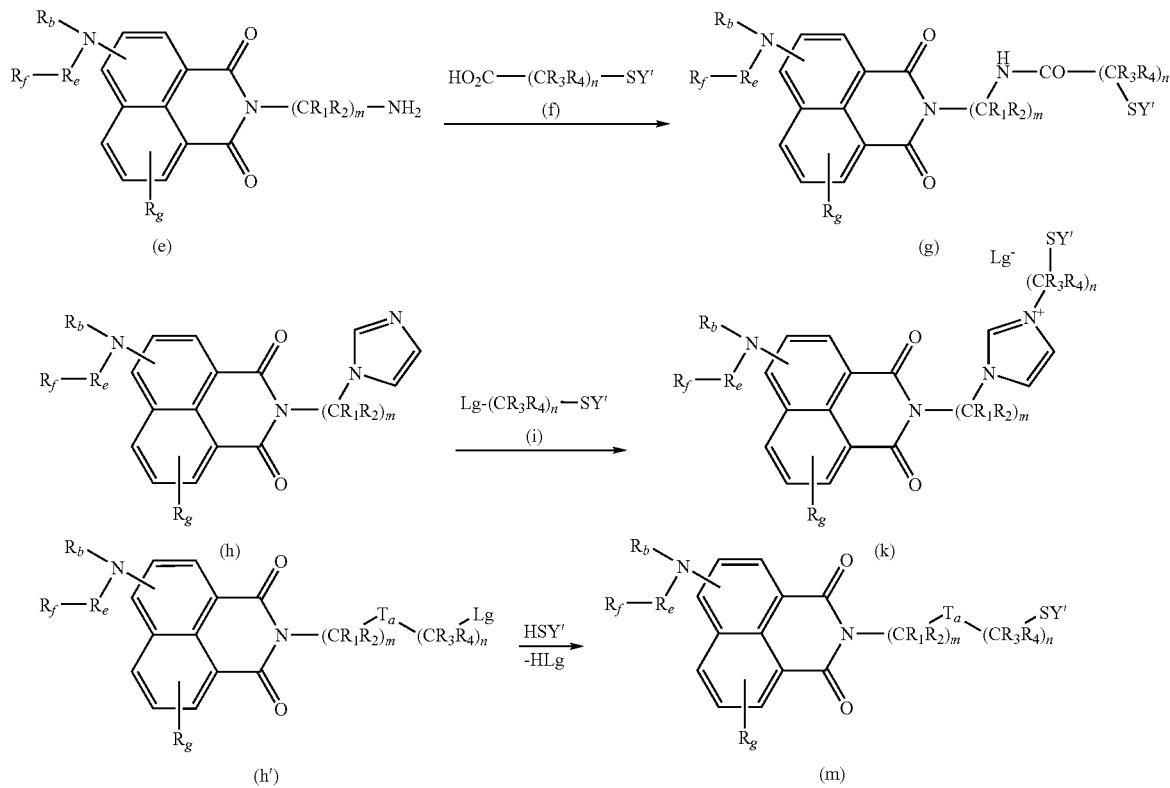

with Lg representing a leaving group such as a halogen, for instance chlorine, bromine or iodine, or a mesylate or tosylate group, particularly bromine or chlorine.

More particularly, a nucleofuge leaving group may be substituted with a thiourea group (S=C(NRR)NRR) so as to generate the isothiouronium. For example, if the thiourea group is a thioimidazolinium (β), the reaction scheme is the following:

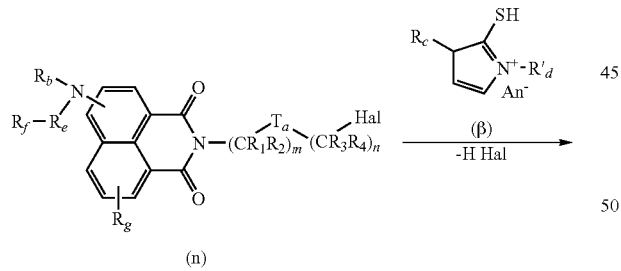

-continued

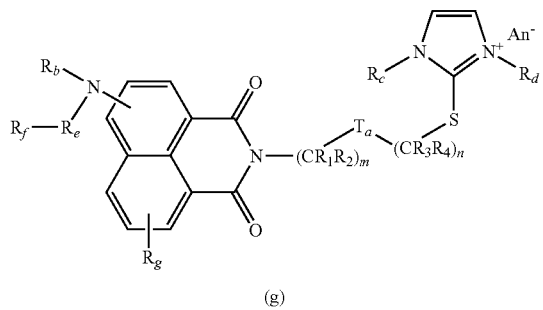

Another variant is to use a thiolactane so as to generate an amide bond $T_a$ as illustrated by the scheme below:

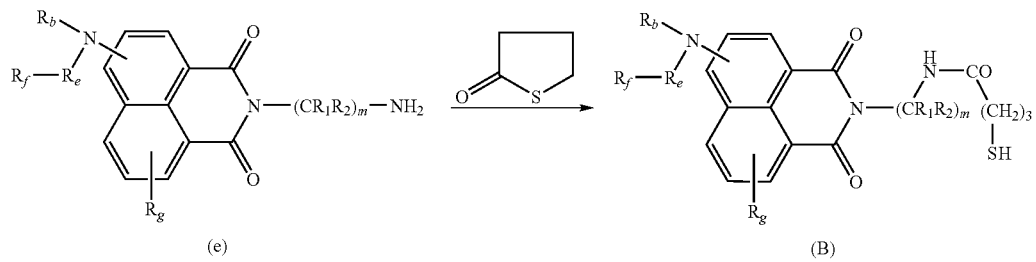

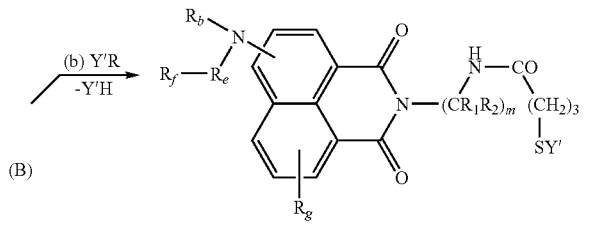

(B)

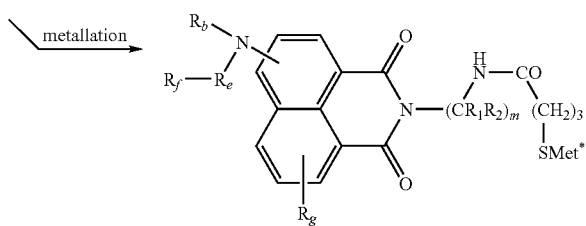

One alternative is to start from a maleic derivative reactant (r) and to generate the naphthylimide part by condensation of an amine derivative nucleophile (s) comprising the protected thiol part, so as to give the dye of the invention of formula (VI):

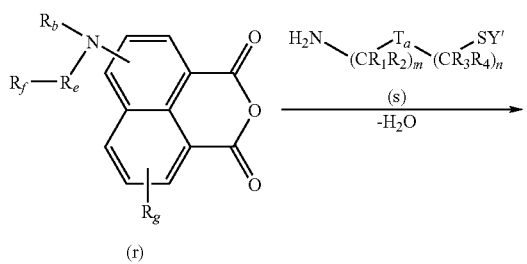

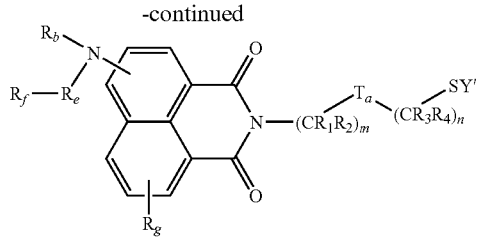

One synthesis variant is to combine, with the first pathway above, two equivalents of the nucleophilic reactant (c) and a dielectrophilic disulphide reactant (t) so as to generate, after condensation, the dichromophore disulphide product (Ia), it being possible for the latter to undergo a reduction so as to form the heterocyclic fluorescent thiol dye (a) which, in turn, can either be protected so as to form the protected thiol fluorescent dye (V') or be metallated with an alkali metal so as to give the metallated heterocyclic thiol fluorescent dye (V")

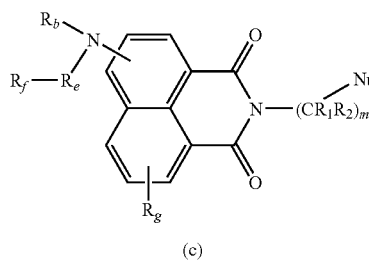

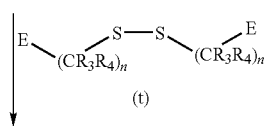

-continued

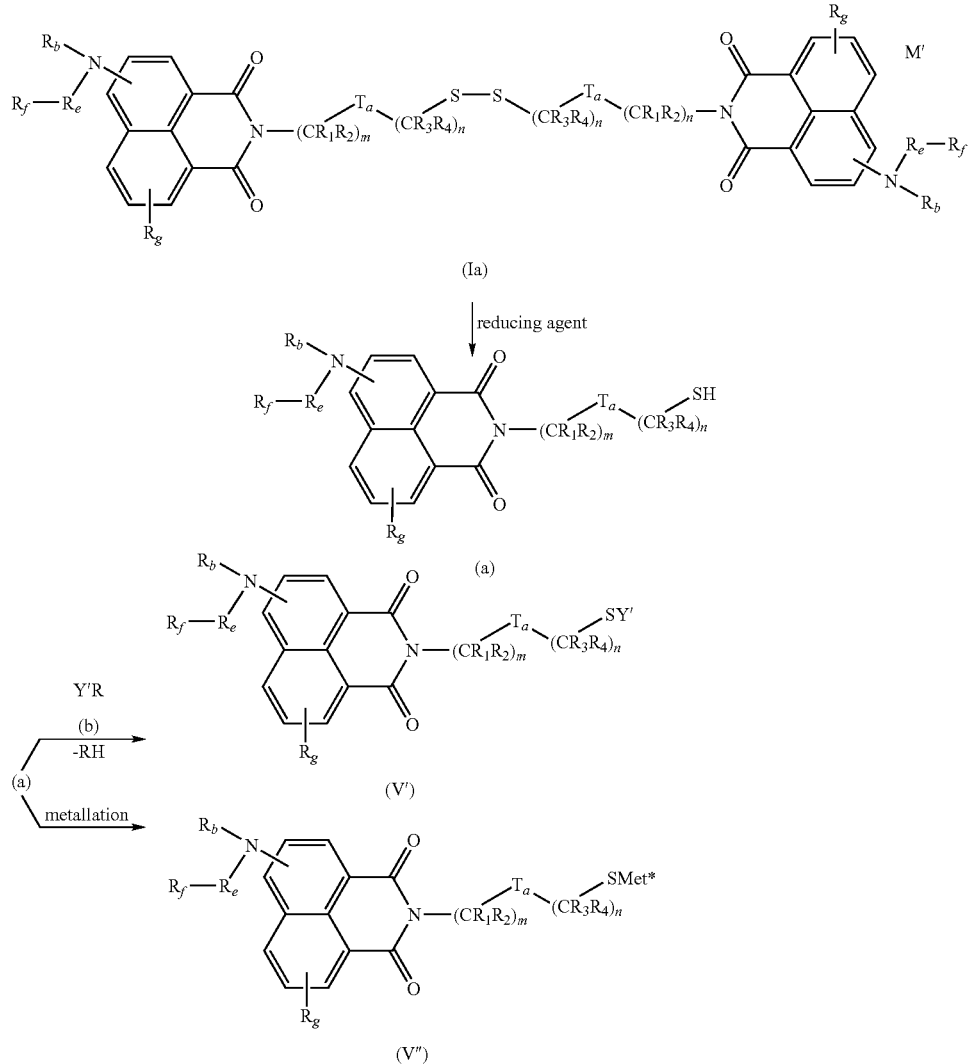

(Ia)

(a)

(V')

(V'')

The protected thiol dyes of formula (VI) can be synthesized in two stages. The first stage consists in preparing the nonprotected thiol dye (a') according to the methods known to those skilled in the art, for instance "*Thiols and organic Sulfides*", "*Thiocyanates and Isothiocyanates, organic*", Ullmann's Encyclopedia, Wiley-VCH, Weinheim, 2005. In addition, the second step consists in protecting the thiol function according to the conventional methods known to those skilled in the art, so as to give the protected thiol dyes of formula (VI') and (V''). By way of example, for protecting the thiol function —SH of the thiol dye, use may be made of the methods of the books "*Protective Groups in Organic Synthesis*", T. W. Greene, John Willey & Sons, Ed., NY, 1981, pp. 193-217; "*Protecting Groups*", P. Kocienski, Thieme, 3rd Ed. 2005, chap. 5.

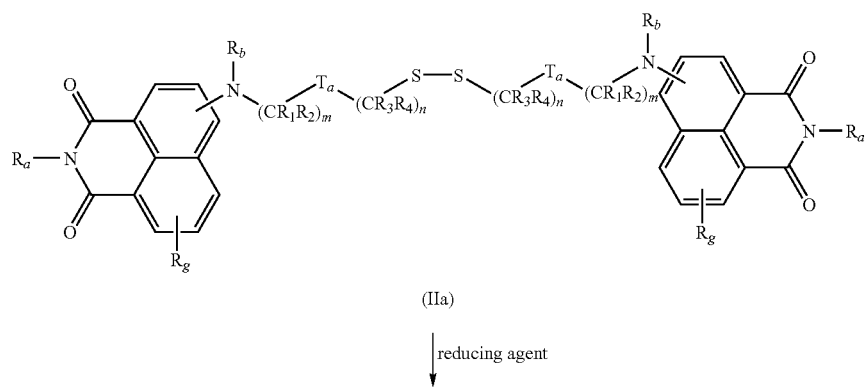

(IIa)

reducing agent

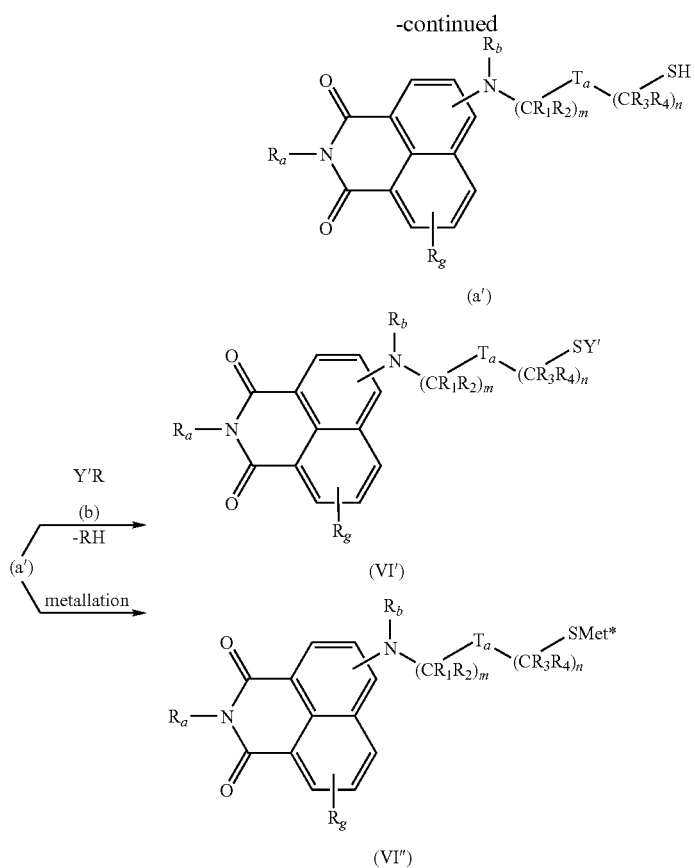

This method can be illustrated by means of the method consisting (i) in generating thiol fluorescent dyes of formula (d') by reduction of a two-chromophore fluorescent dye bearing a disulphide function —S—S— such as (c') and ii) in protecting, according to the conventional methods, said thiol function of (d') with the reactant (b) Y'R, so as to give the protected thiol fluorescent dyes of formula (VI'). The thiol compound (d') may also be metallated with an alkali metal or alkaline earth metal Met* so as to give the thiolate fluorescent dye of formula (VI"), see the scheme above.

For example, more specifically, it is possible to obtain the derivatives of formula (VI) with $T_a$ representing a cationic heterocyclic group, as follows:

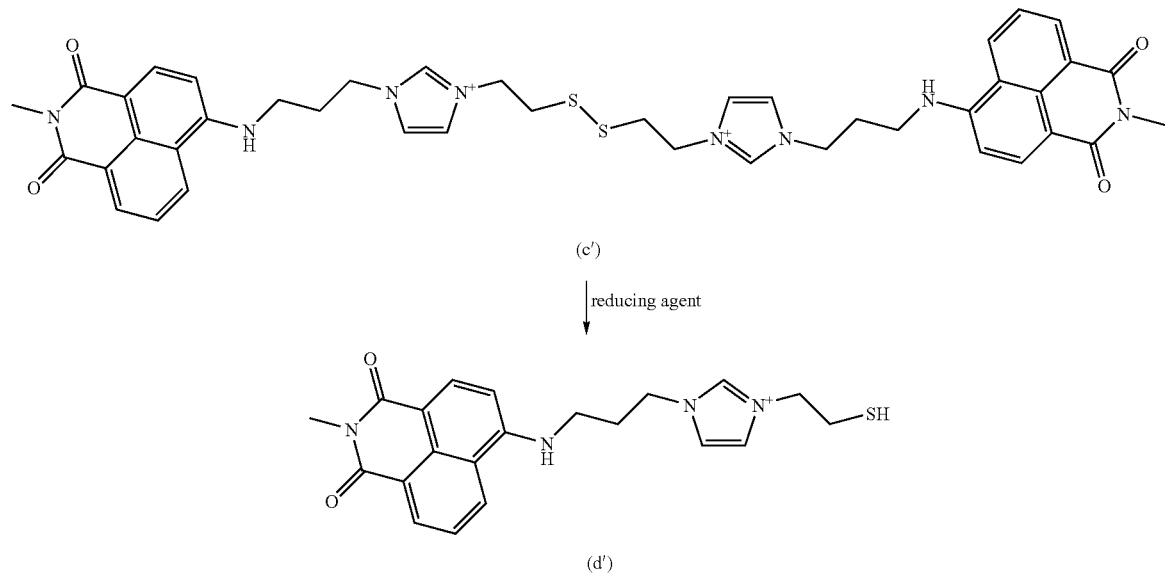

-continued

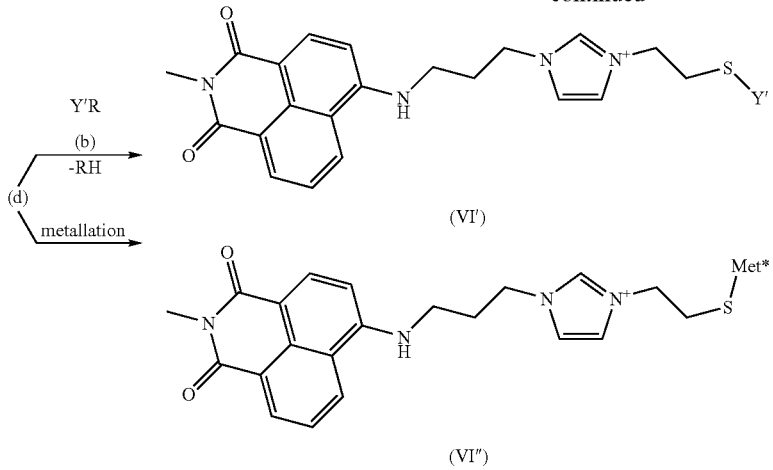
(VI')
(VI'')

According to another possibility, the compounds of formula (VI') can be synthesized using a naphthylimide reactant halogenated (e') on the naphthyl part of said reactant, which can undergo the nucleophilic attack from the amine reactant (f') bearing the nucleophilic group, so as to give the reaction intermediate (g'). The latter can condense with a thiol derivative bearing an electrophilic group (h'), so as to give the fluorescent dye of formula (VI'):

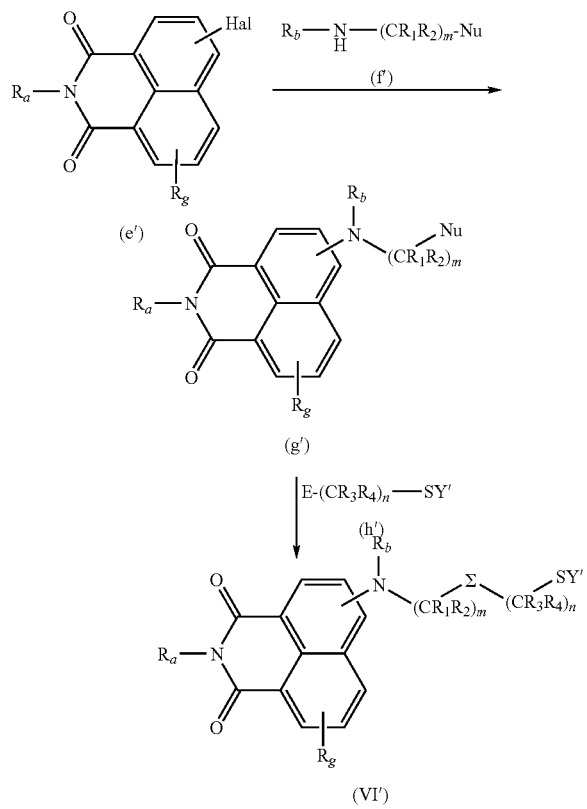

Nu representing a nucleophilic group; E representing an electrophilic group; and Σ the bond generated after attack by the nucleophile on the electrophile. For the first stage of this synthesis, this type of nucleophilic substitution is described in the literature, for example *Dyes & Pigments*, 45, (2000) 125-129; and *J. Chem. Soc Perk Trans* 2 (1990) 837-842.

Another alternative is to use a thiolactone as follows starting from (g') so as to give the dye (B), which can itself be protected or metallated:

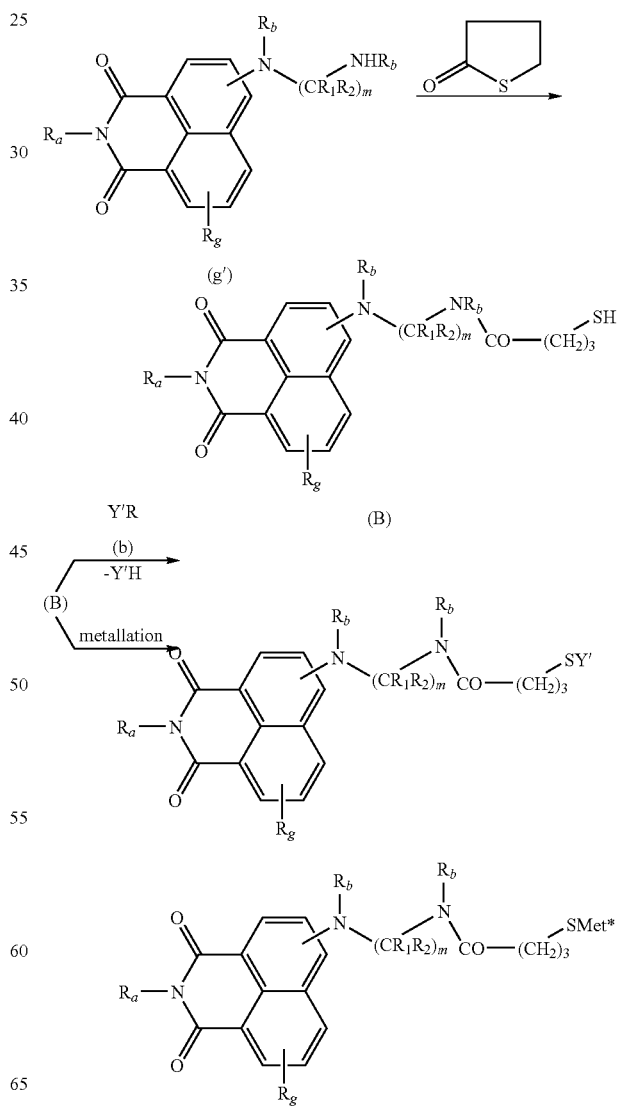

The thiol fluorescent dyes formed may be converted to —SY' protected thiol fluorescent dyes by protection of the —SH thiol using conventional protecting groups. The thiol fluorescent dyes are metallated by also using the conventional methods known to those skilled in the art, such as those described in *Advanced Organic Chemistry*, "Reactions, Mechanisms and Structures", J. March, 4th ed. John Willey & Sons, NY, 1992.

The dissymmetrical disulphide dyes of formula (I) can be synthesized in a single stage by reacting a nonprotected thiol fluorescent dye with a protected thiol fluorescent dye of formula (V) so as to form the dissymmetrical disulphide dye of formula (I)

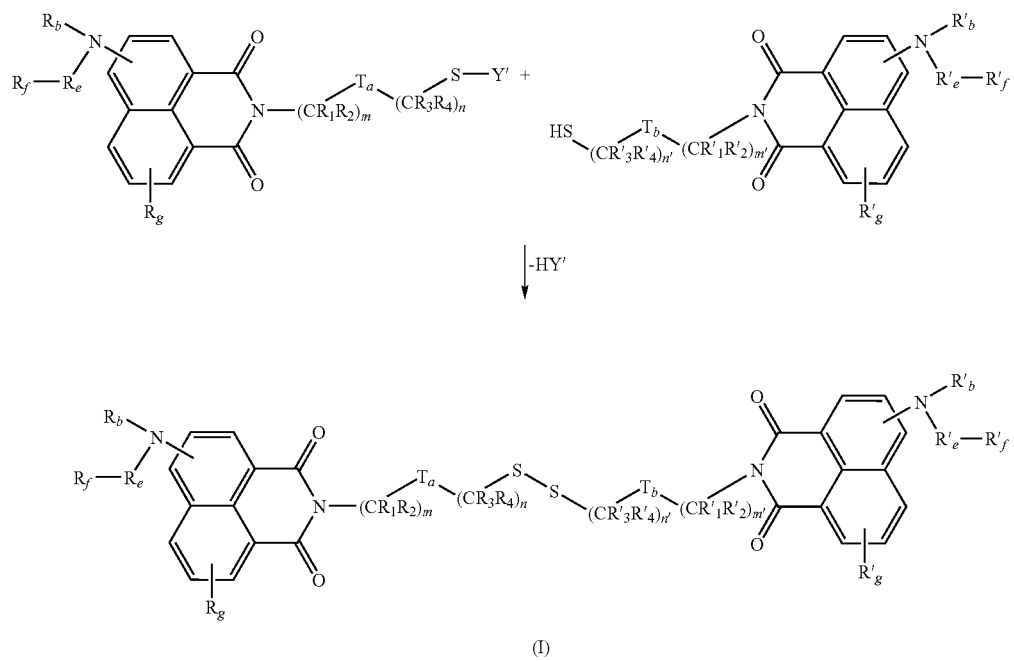

with $R_b$, $R'_b$, $R_e$, $R'_e$, $R_f$, $R'_f$, $R_g$, $R'_g$, m, m', n, n', Ta and Tb as defined above; Y' represents a thiol-function-protecting group.

The dissymmetrical disulphide dyes of formula (II) can be synthesized in a single step by reacting a nonprotected thiol fluorescent dye with a protected thiol fluorescent dye of formula (VI) so as to form the dissymmetrical disulphide dye of formula (II).

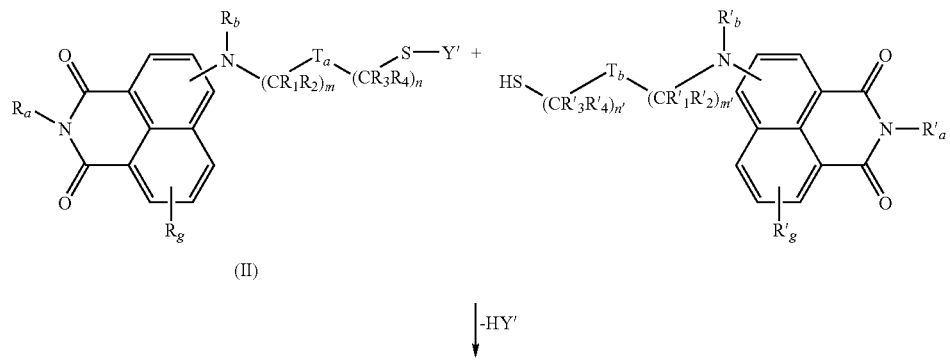

-continued

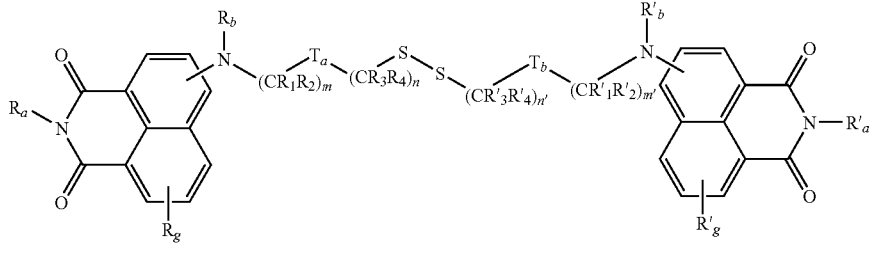

(II)

with $R_a$, $R'_a$, $R_b$, $R'_b$, $R_g$, $R'_g$, $R_1$, $R'_1$, $R_2$, $R'_2$, $R_3$, $R'_3$, $R_4$, $R'_4$, m, m', n, n', $T_a$ and $T_b$ as defined above; Y' represents a thiol-function-protecting group.

The dissymmetrical disulphide dyes of formula (III) can be synthesized in a single step by reacting a protected thiol fluorescent dye with a nonprotected thiol compound so as to form the disulphide dye of formula (III).

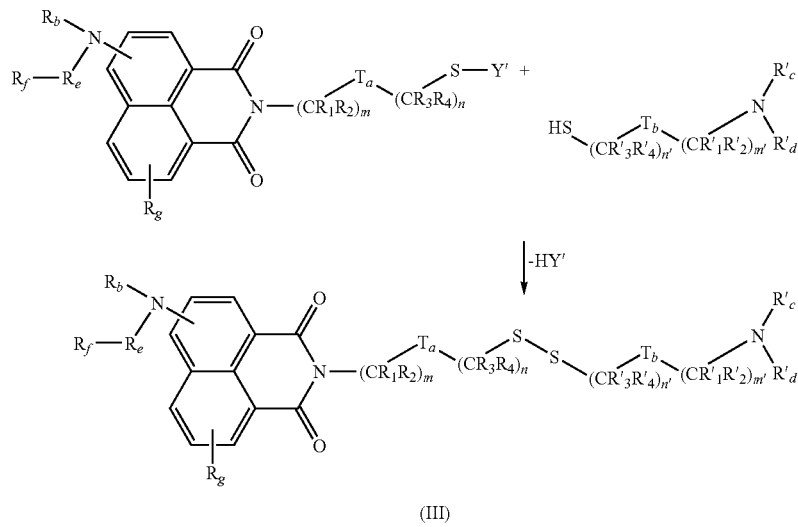

(III)

with $R_b$, $R'_b$, $R_e$, $R'_e$, $R_f$, $R'_f$, $R_g$, $R'_g$, $R'_c$, $R'_d$, $R_1$, $R'_1$, $R_2$, $R'_2$, $R_3$, $R'_3$, $R_4$, $R'_4$, m, m', n, n', $T_a$ and $T_b$ as defined above; Y' represents a thiol-function protecting group.

The dissymmetrical disulphide dyes of formula (IV) can be synthesized in a single step by reacting a protected thiol fluorescent dye with a nonprotected thiol compound so as to form the disulphide dye of formula (IV).

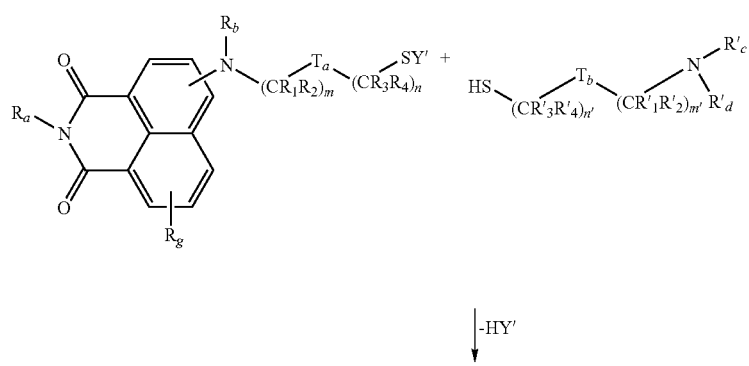

|-HY'

-continued

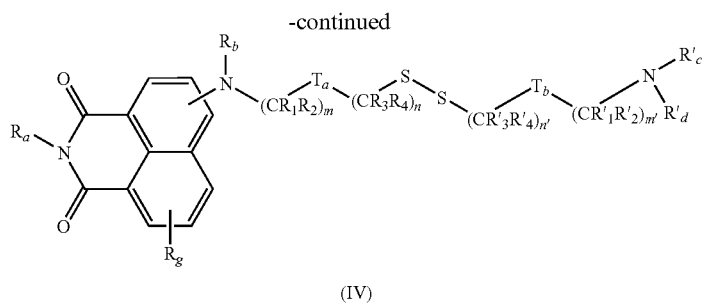

(IV)

with $R_a$, $R'_a$, $R_b$, $R'_b$, $R'_c$, $R'_d$, $R_g$, $R'_g$, $R_1$, $R'_1$, $R_2$, $R'_2$, $R_3$, $R'_3$, $R_4$, $R'_4$, m', n, n', $T_a$ and $T_b$ as defined above; Y' represents a thiol-function-protecting group.

The protected thiol dyes can be deprotected by conventional routes such as those described in the books "*Protective Groups in Organic Synthesis*", T. W. Greene, John Willey & Sons ed., NY, 1981; "*Protecting Groups*", P. Kocienski, Thieme, 3rd ed., 2005.

Reference may be made to the book *Advanced Organic Chemistry*, "Reactions, Mechanisms and Structures", J. March, 4th ed. John Willey & Sons, 1992 or T. W. Greene "*Protective Groups in Organic Synthesis*", for further details on the operating conditions used for the processes mentioned above.

The thiol fluorescent dyes formed can be converted to —SY' protected thiol fluorescent dyes by protection of the —SH thiol using conventional protecting groups. The thiol fluorescent dyes are metallated by also using the conventional methods known to those skilled in the art, such as those described in *Advanced Organic Chemistry*, "Reactions, Mechanisms and Structures", J. March, 4th ed. John Willey & Sons, NY, 1992.

The protected thiol dyes can be deprotected by conventional routes such as those described in the books "*Protective Groups in Organic Synthesis*", T. W. Greene, John Willey & Sons ed., NY, 1981; "*Protecting Groups*", P. Kocienski, Thieme, 3rd ed., 2005.

The composition of the invention contains at least one fluorescent dye of formulae (I) to (VI). In addition to the presence of at least one fluorescent dye of formulae (I) to (VI), the composition of the invention may also contain a reducing agent. This reducing agent may be chosen from thiols, for example cysteine, homocysteine or thiolactic acid, the salts of these thiols, the phosphines, the bisulphite, the sulphites, thioglycolic acid, and also its esters, in particular glycerol monothioglycolate, and thioglycerol. This reducing agent may also be chosen from borohydrides and derivatives thereof, for instance the salts of borohydride, of cyanoborohydride, or triacetoxyborohydride or of trimethoxyborohydride: sodium salts, lithium salts, potassium salts, calcium salts, quaternary ammonium (tetramethylammonium, tetraethylammonium, tetra-n-butylammonium or benzyltriethylammonium) salts; catechol borane.

The dye composition that can be used in the invention generally contains an amount of fluorescent dye of formulae (I) to (VI) of between 0.001% and 50% relative to the total weight of the composition. Preferably, this amount is between 0.005% and 20% by weight, and even more preferably between 0.01% and 5% by weight, relative to the total weight of the composition.

The dye composition may also contain additional direct dyes. These direct dyes are, for example, chosen from neutral, acidic or cationic nitrobenzene direct dyes, neutral, acidic or cationic azo direct dyes, tetraazapentamethine dyes, neutral, acidic or cationic quinone, in particular anthraquinone dyes, azine direct dyes, triarylmethane direct dyes, indoamine direct dyes and natural direct dyes.

Among the natural direct dyes, mention may be made of lawsone, juglone, alizarin, purpurin, carminic acid, kermesic acid, purpurogallin, protocatechaldehyde, indigo, isatin, curcumin, spinulosin and apigenindin. Extracts or decoctions containing these natural dyes, and in particular poultices or henna-based extracts, may also be used.

The dye composition may contain one or more oxidation bases and/or one or more couplers conventionally used for dyeing keratin fibres.

Among the oxidation bases, mention may be made of para-phenylenediamines, bisphenylalkylenediamines, para-aminophenols, bis-para-aminophenols, ortho-aminophenols, heterocyclic bases, and addition salts thereof.

Among these couplers, mention may in particular be made of meta-phenylenediamines, meta-aminophenols, meta-diphenols, naphthalene couplers, heterocyclic couplers, and addition salts thereof.

The coupler(s) is (are) each generally present in an amount of between 0.001% and 10% by weight of the total weight of the dye composition, preferably between 0.005% and 6%.

The oxidation base(s) present in the dye composition is (are) in general each present in an amount of between 0.001% and 10% by weight of the total weight of the dye composition, preferably between 0.005% and 6% by weight.

In general, the addition salts of the oxidation bases and of the couplers that can be used in the context of the invention are in particular chosen from addition salts with an acid, such as hydrochlorides, hydrobromides, sulphates, citrates, succinates, tartrates, lactates, tosylates, benzenesulphonates, phosphates and acetates, and addition salts with a base, such as hydroxides of an alkali metal such as sodium or potassium, aqueous ammonia, amines or alkanolamines.

The medium suitable for dyeing, also called dye support, is a cosmetic medium generally constituted of water or of a mixture of water and at least one organic solvent. By way of organic solvent, mention may, for example, be made of $C_1$-$C_4$ lower alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether, and also aromatic alcohols such as benzyl alcohol or phenoxyethanol, and mixtures thereof.

The solvents, when they are present, are preferably present in proportions of preferably between 1% and 40% by weight approximately, relative to the total weight of the dye composition, and even more preferably between 5% and 30% by weight approximately.

According to one variant, the invention contains a reducing agent capable of reducing the disulphide bonds of keratin and/or the disulphide bonds of the fluorescent dyes of formulae (I) to (IV). This reducing agent is as defined above.

The dye composition may also contain various adjuvants conventionally used in hair-dyeing compositions, such as anionic, cationic, nonionic, amphoteric or zwitterionic surfactants or mixtures thereof, anionic, cationic, nonionic, amphoteric or zwitterionic polymers, or blends thereof, mineral or organic thickeners, and in particular anionic, cationic, nonionic and amphoteric associative polymer thickeners, antioxidants, penetrating agents, sequestering agents, fragrances, buffers, dispersing agents, conditioning agents such as, for example, modified or unmodified, volatile or nonvolatile silicones, such as amino silicones, film-forming agents, ceramides, preservatives, opacifiers or conductive polymers.

The above adjuvants are in general present in an amount, for each of them, of between 0.01% and 20% by weight relative to the weight of the composition.

Of course, those skilled in the art will take care to select this or these possible additional compounds in such a way that the advantageous properties intrinsically associated with the dye composition in accordance with the invention are not, or are not substantially, impaired by the addition(s) envisaged.

The pH of the dye composition is generally between 4 and 14 approximately, and preferably between 5 and 11 approximately. It may be adjusted to the desired value by means of acidifying or basifying agents normally used in the dyeing of keratin fibres or else by means of conventional buffer systems.

Among the acidifying agents, mention may, by way of example, be made of mineral or organic acids, such as hydrochloric acid, orthophosphoric acid, sulphuric acid, carboxylic acids, for instance acetic acid, tartaric acid, citric acid or lactic acid, or sulphonic acids.

Among the basifying agents, mention may, by way of example, be made of aqueous ammonia, alkali carbonates, alkanolamines such as mono-, di- and triethanolamines, and also derivatives thereof, sodium hydroxide or potassium hydroxide and the compounds of formula (γ) below:

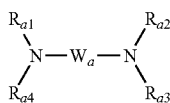

in which $W_a$ is a propylene residue optionally substituted with a hydroxyl group or a $C_1$-$C_4$ alkyl radical; $R_{a1}$, $R_{a2}$, $R_{a3}$ and $R_{a4}$, which may be identical or different, represent a hydrogen atom, a $C_1$-$C_4$ alkyl radical or a $C_1$-$C_4$ hydroxyalkyl radical.

The dye composition may be in various forms, such as in the form of a liquid, a cream or a gel, or in any other form suitable for dyeing keratin fibres, and in particular the hair.

According to a specific embodiment in the process of the invention, a reducing agent may be applied as a pretreatment before the application of the composition containing at least one fluorescent dye of formulae (I) or (VI).

This reducing agent may be chosen from thiols, for example cysteine, homocysteine or thiolactic acid, the salts of these thiols, the phosphines, the bisulphite, the sulphites, thioglycolic acid, and also its esters, in particular glyceryl monothioglycolate, and thioglycerol. This reducing agent may also be chosen from borohydrides and derivatives thereof, for instance the salts of borohydride, of cyanoborohydride, of triacetoxyborohydride or of trimethoxyborohydride: sodium salts, lithium salts, potassium salts, calcium salts, quaternary ammonium (tetramethylammonium, tetraethylammonium, tetra-n-butylammonium, benzyltriethylammonium) salts; catechol borane.

This pretreatment may be of short duration, in particular from 0.1 second to 30 minutes, preferably from 1 minute to 15 minutes, with a reducing agent as mentioned above.

According to another process, the composition comprising at least one fluorescent dye of formulae (I) to (VI) also contains at least one reducing agent as defined above. This composition is then applied to the hair.

When the fluorescent dye of formula (V) or (VI) comprises a thiol-function-protecting group Y, the process of the invention may be preceded by a deprotection step aimed at restoring the SH function in situ.

By way of example, it is possible to deprotect the S—Y function with a Y protecting group by adjusting the pH as follows:

| Y: Protecting group | Deprotection |
|---|---|
| alkylcarbonyl | pH > 9 |
| arylcarbonyl | pH > 9 |
| alkoxycarbonyl | pH > 9 |
| aryloxycarbonyl | pH > 9 |
| arylalkoxycarbonyl | pH > 9 |
| (di)(alkyl)aminocarbonyl | pH > 9 |
| (alkyl)arylaminocarbonyl | pH > 9 |
| optionally substituted aryl, such as phenyl | pH > 9 |
| 5-,6- or 7-membered monocyclic heteroaryl such as oxazolium | pH > 9 |
| 8- to 11-membered bicyclic heteroaryl, such as benzoimidazolium or benzoxazolium | pH > 9 |

The deprotection step can also be carried out during a hair pretreatment step, for instance reducing pretreatment of the hair.

According to one variant, the reducing agent is added to the dye composition containing at least one fluorescent dye of formulae (I) to (VI) at the time of use.

According to another process, the composition comprising at least one fluorescent dye of formulae (I) to (VI) also contains at least one reducing agent as defined above. This composition is then applied to the hair.

According to another variant, the reducing agent is applied as a post-treatment, after the application of the composition containing at least one fluorescent dye of formulae (I) to (VI). The duration of the post-treatment with the reducing agent may be short, for example from 0.1 second to 30 minutes, preferably from 1 minute to 15 minutes, with a reducing agent as described above. According to a specific embodiment, the reducing agent is an agent of thiol or borohydride type as described above.

A specific embodiment of the invention relates to a process in which the fluorescent dye of formulae (I) to (VI) can be applied directly to the hair without reducing agents, free of reducing pretreatment or reducing post-treatment.

In the dyeing process, another variant is to apply the fluorescent dye of formula (I) to (VI) at the same time as the reducing agent.

A treatment with an oxidizing agent may optionally be combined. Any type of oxidant conventional in the field may be used. Thus, it may be chosen from hydrogen peroxide, urea peroxide, alkali metal bromates, persalts such as perborates and persulphates, and also enzymes, among which mention may be made of peroxidases, 2-electron oxidoreductases such as uricases and 4-electron oxygenases such as laccases. The use of hydrogen peroxide is particularly preferred.

This oxidizing agent can be applied to the fibres before or after the application of the composition containing at least one fluorescent dye of formulae (I) to (VI).

The application of the dye composition according to the invention is generally carried out at ambient temperature. It may, however, be carried out at temperatures ranging from 20 to 180° C.

A subject of the invention is also a multicompartment device or dyeing kit in which a first compartment contains a dye composition comprising at least one fluorescent dye of formulae (I) to (VI) and a second compartment contains a reducing agent capable of reducing the disulphide functions of keratin materials.

One of these compartments may also contain one or more other dyes of direct dye or oxidation dye type.

The invention also relates to a multicompartment device in which a first compartment contains a dye composition comprising at least one fluorescent dye of formulae (I) to (VI); a second compartment contains a reducing agent capable of reducing the disulphide bond of keratin materials and/or the disulphide bonds of disulphide dyes (I) to (IV); and a third compartment contains an oxidizing agent.

Alternatively, the dyeing device contains a first compartment containing a dye composition which comprises at least one protected thiol fluorescent dye of formulae (V) or (VI) and a second compartment containing an agent capable of deprotecting the protected thiol so as to free the thiol.

BRIEF DESCRIPTION OF THE DRAWING

FIG. 1 shows the reflectance of locks treated with compound 1 at application and after 5 shampooing operations.

Each of the devices mentioned above may be equipped with a means for delivering the desired mixture to the hair, for example such as the devices described in patent FR 2 586 913.

The examples which follow serve to illustrate the invention without, however, being limiting in nature.

The thiol fluorescent dyes of the examples hereinafter have been entirely characterized by conventional spectroscopic and spectrometric methods.

EXAMPLES

Synthesis Examples

Example 1

Synthesis of 3,3'-{disulphanydiylbis[ethane-2,1-diyl (1,3-dioxo-1H-benzo[de]isoquinoline-2,6(3H)-diyl) imino}bis(N,N,N-trimethylpropan-1-aminium) sulphate [1]

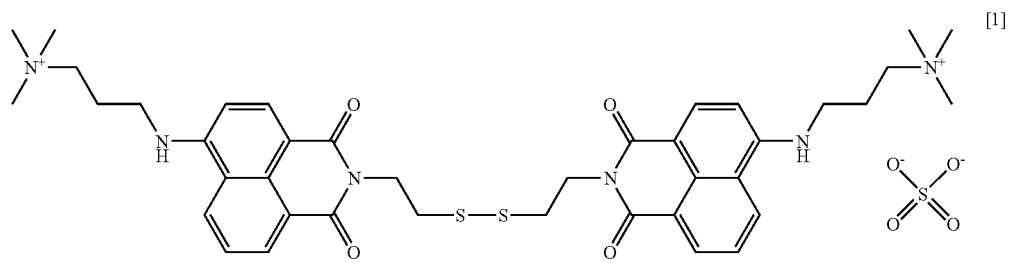

Synthesis scheme

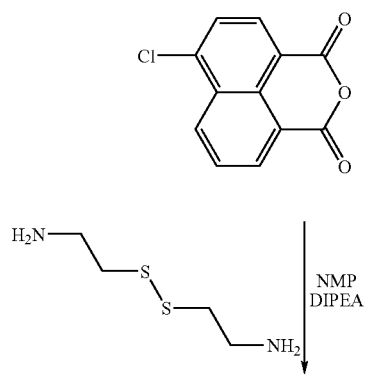

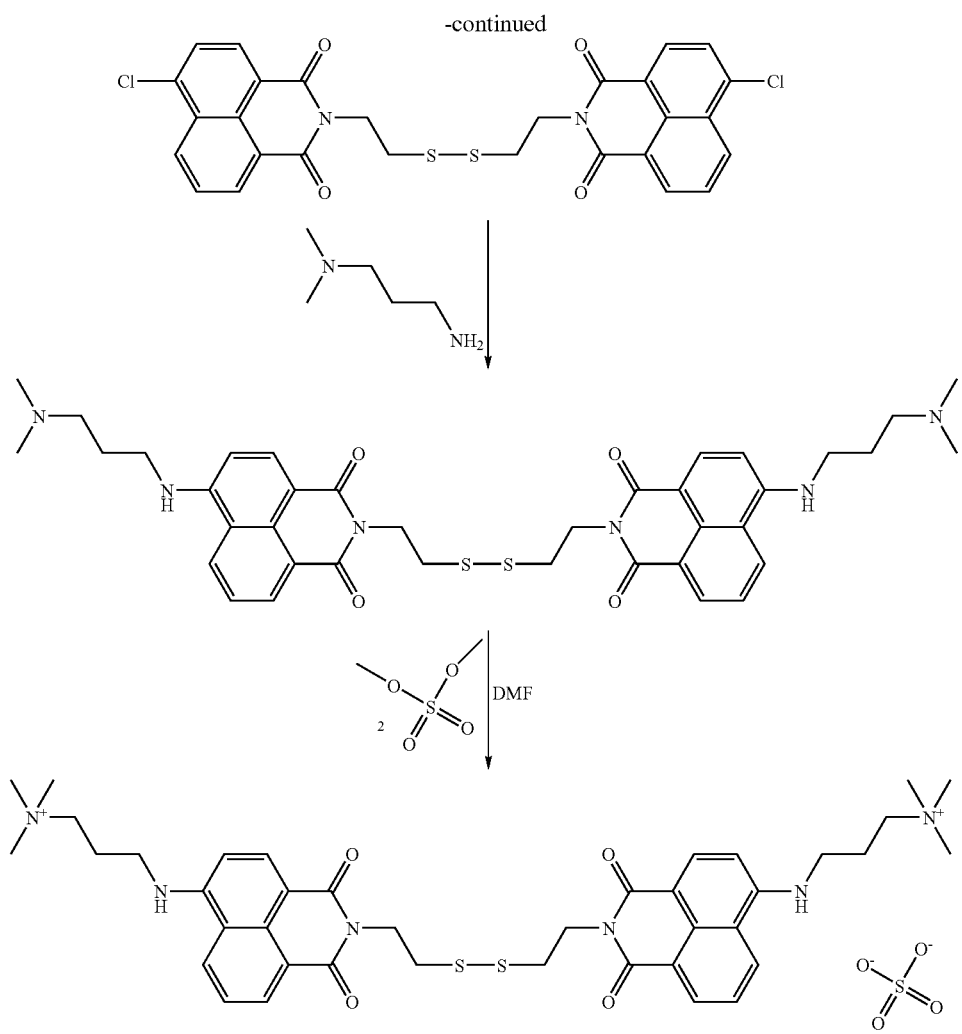

Stage 1: Synthesis of 2,2'-(disulphanediyldiethane-2,1-diyl)bis(6-chloro-1H-benzo[de]isoquinoline-1,3(2H)-dione)

9.30 g of 6-chlorobenzo[de]isochromene-1,3-dione purified beforehand by recrystallization with hot toluene, and dried in an oven at 66° C., 4.46 g of cystamine hydrochloride and 50 ml of N-methylpyrrolidinone (NMP) are mixed, and then 5.5 g of diisopropylamine (DIPEA) are added. The reaction mixture is heated at 120° C. for 2 h. 50 ml of NMP are added to the mixture and the heating is continued for 3 h with stirring. The stirring is stopped for 7 hours. 100 ml of water are added to the reaction mixture, and the white precipitate obtained is filtered off, washed with 3 times 100 ml of water and then dried in an oven. 9.01 g of white solid are recovered.

Stage 2: Synthesis of 2,2'-(disulphanediyldiethane-2,1-diyl)bis[6-{[3-dimethylamino)propyl]amino}-1H-benzo[de]isoquinoline-1,3(2H)-dione]

4 g of 2,2'-(disulphanediyldiethane-2,1-diyl)bis(6-chloro-1H-benzo[de]isoquinoline-1,3(2H)-dione) and 40 ml of N,N-dimethylpropane-1,3-diamine are mixed with stirring and heated at 110° C. for 18 h and then at ambient temperature for 17 h. The precipitate obtained is removed. 500 ml of an EtOH/H$_2$O mixture (1/1) are added to the supernatant, then 200 ml of acetone are added to the precipitate, and the gum obtained is washed with 3 times 100 ml of distilled water and dried in an oven at 66° C. 4.5 g of solid are recovered.

Stage 3: Synthesis of 3,3'-{disulphanediylbis[ethane-2,1-diyl(1,3-dioxo-1H-benzo[de]isoquinoline-2,6(3H)-diyl)imino]}bis(N,N,N-trimethylpropan-1-aminium) sulphate [1]

4 g of 2,2'-(disulphanediyldiethane-2,1-diyl)bis[6-{[3-(dimethylamino)propyl]amino}-1H-benzo[de]isoquinoline-1,3(2H)-dione] in suspension in 50 ml of dimethylformamide (DMF) are stirred. 4 ml of dimethyl sulphate are introduced into the reaction medium, and stirred for 4 h at ambient temperature. The mixture is precipitated from 500 ml of ethyl acetate, and the precipitate is filtered off, washed with 4 times 100 ml of ethyl acetate, then dried under vacuum at 40° C. in the presence of P$_2$O$_5$. 5.91 g of yellow powder are recovered. The analyses indicate that the product is in conformity. $^1$H NMR (400 MHz, DMSO-d6) 2.13 (m, 4H), 3.06 (m, 4H), 3.09 (s, 18H), 3.46 (m, 4H), 4.36 (m, 4H), 6.85 (d, 2H), 7.71 (m, 2H), 7.82 (t, 2H), 8.28 (d, 2H), 8.29 (dd, 2H), 8.45 (dd, 2H).

Example 2

Synthesis of 3-{[1,3-dioxo-2-(2-sulphanylethyl)-2,3-dihydro-1H-benzo[de]isoquinolin-6-yl]amino}-N,N,N-trimethylpropan-1-aminium sulphate [2]

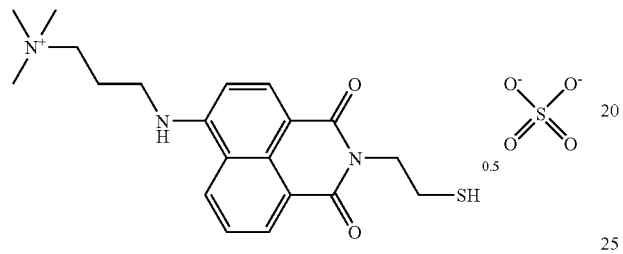

Synthesis of the 3-{[1,3-dioxo-2-(2-sulphanylethyl)-2,3-dihydro-1H-benzo[de]isoquinolin-6-yl]amino}-N,N,N-trimethylpropan-1-aminium salt [2]

84 mg of compound [1] are dissolved in 10 ml of a 1:1 water/ethanol mixture, and 60 mg (2 eq.) of 3-[bis(2-carboxyethyl)phosphino]propanoic acid hydrochloride hydrate in solution in 1 ml of water and 21 mg (4 eq) of sodium bicarbonate in solution in 1 ml of water are added to the mixture. After stirring for 30 minutes at 40° C. under an inert atmosphere, the analyses indicate that the mixture contains very predominantly the expected product [2].

LC-MS analysis: LC-DAD (400-700 nm)
Column: Waters XTerra MS C18 5 μm (4.6×50) mm
Mobile phase: A: water+0.1% formic acid/B: acetonitrile
Linear gradient: T (min) A %/B %: 0 min 95/5; 8 min 0/100
Flow rate: 1 ml/min
Detection: UV diode array λ=400-700 nm
Retention time t=3.8 min
Relative purity >95%
MS (ESI+) m/z=372 corresponds to the mass peak of the cation of the expected product [2].

Synthesis scheme

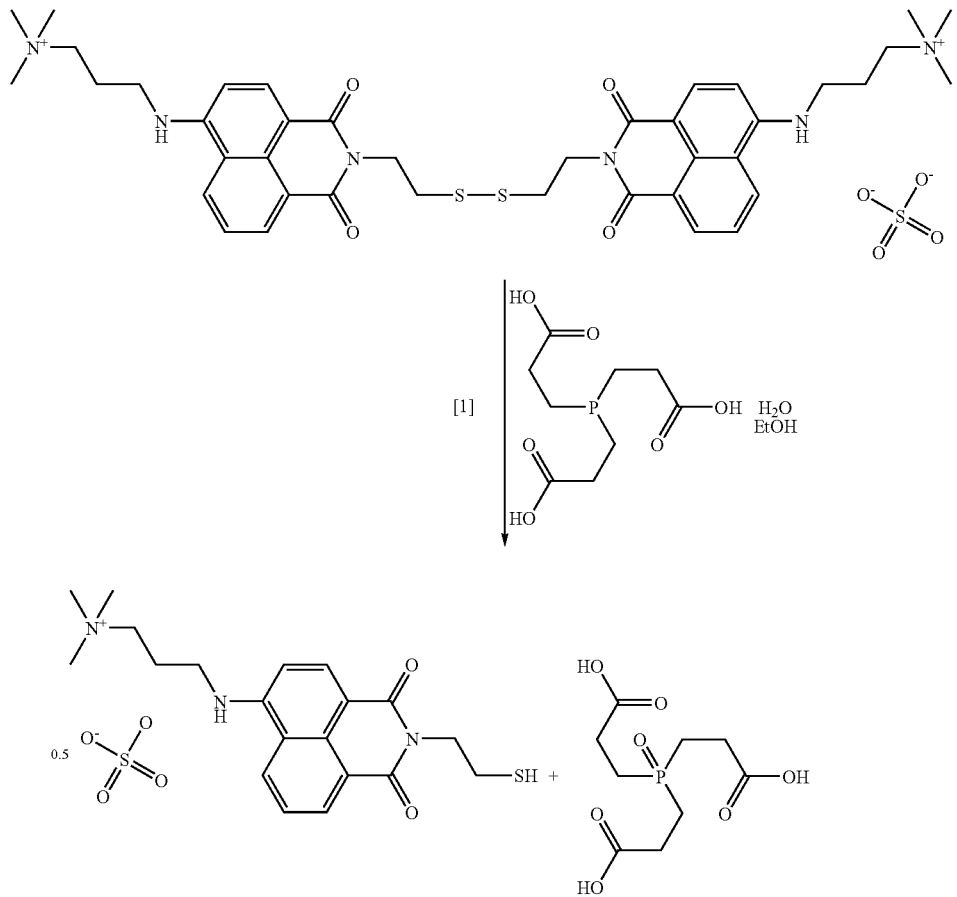

Dyeing Examples

Example 1

Dyeing Process-Compound [1]

| Preparation of a composition A | |
|---|---|
| Disulphide dye [1] | $10^{-3}$ mol % |
| Benzyl alcohol | 4 g |
| Polyethylene glycol 60 EO | 6 g |
| Hydroxyethylcellulose | 0.7 g |
| Alkylpolyglucoside in an aqueous solution containing 65% AM | 4.5 g |
| Demineralized water | qs 100 g |
| Preparation of a composition B | |
| Thioglycolic acid | 1 M |
| Sodium hydroxide | qs pH 8.5 |
| Demineralized water | qs 100 g |

At the time of use, compositions A (9 ml) and B (1 ml) are mixed, then the mixture obtained is applied to a lock of 1 g of dark hair (tone height 4) for 30 minutes at ambient temperature (the locks are turned over and reimpregnated after 15 minutes).

After rinsing with running water and drying, lightening of the hair thus treated is observed: the lock of tone height 4 has become visually lighter than untreated control locks.

Example 2

Dyeing Process with Compound [2]

10 ml of fresh solution of compound [2] of the synthesis example are applied to a lock of 1 g of hair of tone height 4 placed at the bottom of a bowl for 30 minutes at ambient temperature (the locks are turned over and reimpregnated after 15 minutes).

The locks are subsequently rinsed with running water and dried.

After dyeing, the lock of tone height 4 has become visually lighter than untreated control locks.

Remanence with Respect to Successive Shampooing Operations:

The locks thus treated are divided into two, half are subjected to 5 successive shampooing operations according to a cycle which comprises wetting the locks with water, washing with a conventional shampoo, rinsing with water, followed by drying.

Visual Observations

During the shampooing operations, there is no visible bleeding, the shampoo foam and the rinsing water are not coloured.

The colour observed is conserved and the lightening effect remains visible on the hair of tone height 4 thus treated.

Results in the L*a*b* System:

The colour of the locks before and after the 5 washes was evaluated in the L*a*b* system by means of a MINOLTA® CM 2600D spectrophotometer, (illuminant D65).

In this L*a*b* system, L* represents the luminosity, a* indicates the green/red colour axis and b* the blue/yellow colour axis. The higher the value of L, the lighter or weaker a colour, conversely, the lower the value of L, the darker or much stronger the colour. The higher the value of a*, the redder the shade, and the higher the value of b*, the more yellow the shade.

The variation in colouring between the TH4 (tone height 4) dyed and washed locks of hair is measured by ($\Delta E$) according to the following equation:

$$\Delta E = \sqrt{(L^* - L_0^*)^2 + (a^* - a_0^*)^2 + (b^* - b_0^*)^2}$$

In this equation, L*, a* and b* represent the values measured before dyeing, and $L_0^*$, $a_0^*$ and $b_0^*$ represent the values measured before dyeing (or shampooing).

The greater the value of $\Delta E$, the greater the difference in colour between TH4 locks and the coloured locks.

| Treatment with the fluorescent dye on the TH4 locks | $\Delta E$ |
|---|---|
| After application of compound 1 according to the invention | 4.39 |
| After application of compound 1 according to the invention and after 5 successive shampooing operations | 3.63 |
| After application of compound 2 according to the invention | 3.00 |
| After application of compound 2 according to the invention and after 5 successive shampooing operations | 1.45 |

The results in the table above show that the coloring changes very little after 5 shampooing operations. Thus, the coloring and the lightening effect on the hair remains virtually unchanged, which shows a very good resistance to shampooing of the dyes of the invention.

Reflectance Results:

The lightening effectiveness of the compositions in accordance with the invention and the remanance of said compositions with respect to successive shampooing operations were expressed as a function of the reflectance of the hair. These reflectances are compared with the reflectance of a lock of untreated hair of tone height TH4.

The reflectance is measured by means of a KONIKA-MINOLTA® CM 2600d spectrophotocolorimeter apparatus and after irradiation of the hair with visible light in the wavelength range of from 400 to 700 nanometers.

According to FIG. 1, it is noted that the reflectance of a lock of hair treated with a composition according to the invention is greater than that of the untreated hair. The treated locks therefore appear to be lighter.

Furthermore, the results obtained for compound 1 (see FIG. 1) show that the reflectance of the locks of hair of tone height 4, treated with the composition of the invention, change very little after 5 shampooing operations. Thus, the colouring and the lightening effect on the hair remain virtually unchanged, which shows a very good resistance of the dyes of the invention to shampooing operations.

The invention claimed is:

1. At least one fluorescent entity chosen from those of formulae (I), (II), (III), (IV), (V), and (VI):

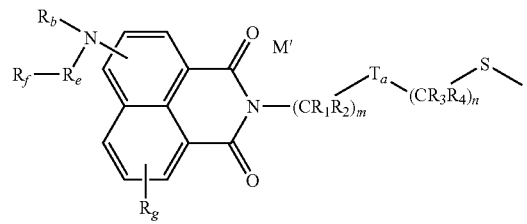

(I)

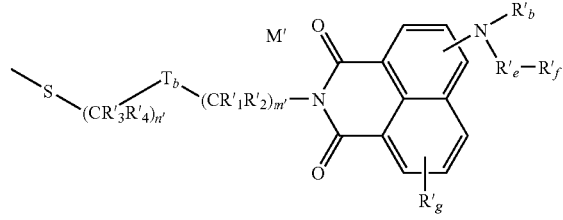

(II)

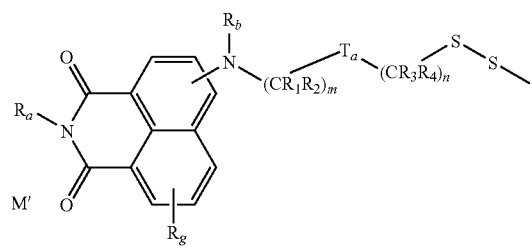

(III)

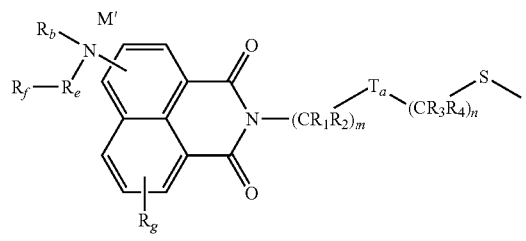

(IV)

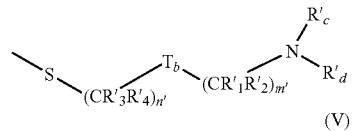

(V)

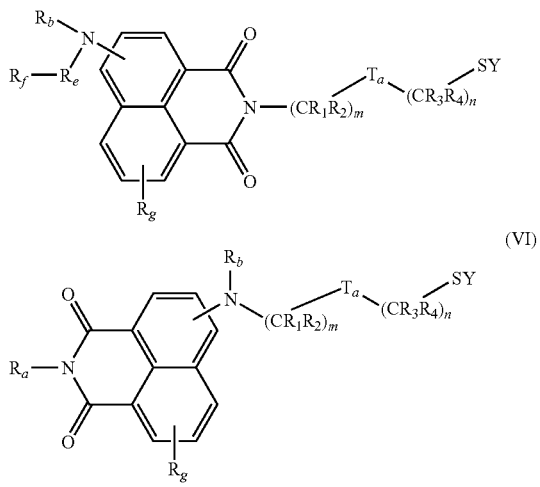

(VI)

the organic and mineral acid salts, optical isomers and geometrical isomers, and the solvates thereof;
wherein:
$R_a$ and $R'_a$, which may be identical or different, represent an aryl($C_1$-$C_4$)alkyl group or a ($C_1$-$C_6$)alkyl group optionally substituted with a hydroxyl group or a (di)($C_1$-$C_4$)(alkyl)amino group, it being possible for said alkyl radicals to form, with the nitrogen atom which bears them, a heterocycle comprising from 5 to 7 members, optionally comprising another heteroatom which may or may not be different from nitrogen;
$R_b$ and $R'_b$, which may be identical or different, represent a hydrogen atom, an aryl($C_1$-$C_4$)alkyl group or a ($C_1$-$C_6$)alkyl group which is optionally substituted;
$R'_c$ and $R'_d$, which may be identical or different, represent a hydrogen atom, an aryl($C_1$-$C_4$)alkyl group or a $C_1$-$C_6$ alkyl group which is optionally substituted;
$R_e$ and $R'_e$, which may be identical or different, represent an optionally unsaturated, linear or branched, divalent ($C_1$-$C_6$)alkylenyl hydrocarbon-based chain;
$R_f$ and $R'_f$, which may be identical or different, represent
i) a quaternary ammonium group (R")(R''')(R'''')N$^+$—, M' where R", R''' and R'''', which may be identical or different, represent a hydrogen atom or a ($C_1$-$C_4$)alkyl group, or else (R")(R''')(R'''')N$^+$— represents an optionally substituted, cationic heteroaryl group, and M' represents an anionic counterion; ii) a hydroxyl group; iii) ($C_1$-$C_6$)(di)(alkyl)amino; or iv) an optionally substituted, noncationic heteroaryl;
$R_g$ and $R'_g$, which may be identical or different, represent a hydrogen or halogen atom, an amino, (di)($C_1$-$C_4$)alkylamino, cyano, carboxyl, hydroxyl, trifluoromethyl, acylamino, $C_1$-$C_4$ alkoxy, $C_2$-$C_4$ (poly)hydroxyalkoxy, ($C_1$-$C_4$)alkylcarbonyloxy ($C_1$-$C_4$)alkoxycarbonyl, ($C_1$-$C_4$)alkylcarbonylamino, acylamino, carbamoyl or ($C_1$-$C_4$)alkylsulphonylamino group, an aminosulphonyl radical, or a ($C_1$-$C_{16}$)alkyl radical optionally substituted with a group chosen from ($C_1$-$C_{12}$)alkoxy, hydroxyl, cyano, carboxyl, amino and (di)($C_1$-$C_4$)alkylamino, or else the two alkyl radicals borne by the nitrogen atom of the amino group form a heterocycle comprising from 5 to 7 members and optionally comprising another heteroatom identical to or different from that of the nitrogen atom;

$R_1$, $R'_1$, $R_2$, $R'_2$, $R_3$, $R'_3$, $R_4$ and $R'_4$, which may be identical or different, represent a hydrogen atom or a ($C_1$-$C_4$)alkyl, ($C_1$-$C_4$)alkoxy, hydroxyl, cyano, carboxyl or (di)($C_1$-$C_4$)(alkyl)amino group, it being possible for said alkyl radicals to form, with the nitrogen atom which bears them, a heterocycle comprising from 5 to 7 members, optionally comprising another heteroatom which may or may not be different from nitrogen;

$T_a$ and $T_b$, which may be identical or different, represent:
  i) a σ covalent bond,
  ii) at least one radical chosen from —$SO_2$—, —O—, —S—, —N(R)—, —$N^+$(R)($R^o$)— and —C(O)—, with R and $R^o$, which may be identical or different, representing a hydrogen atom, a $C_1$-$C_4$ alkyl radical, a $C_1$-$C_4$ hydroxyalkyl radical or an aryl($C_1$-$C_4$)alkyl; or
  iii) a monocyclic, cationic or noncationic, heterocycloalkyl or heteroaryl radical comprising two heteroatoms;

m, m', n and n', which may be identical or different, represent an integer ranging from 0 to 6, wherein the sums m+n and m'+n', which may be identical or different, represent an integer ranging from 1 to 10; and Y represents: i) a hydrogen atom; ii) an alkali metal; iii) an alkaline earth metal; iv) an ammonium group: $N^+R^\alpha R^\beta R^\gamma R^\delta$ or a phosphonium group: $P^+R^\alpha R^\beta R^\gamma R^\delta$ with $R^\alpha$, $R^\beta$, $R^\gamma$ and $R^\delta$, which may be identical or different, representing a hydrogen atom or a ($C_1$-$C_4$) alkyl group; or v) a thiol-function-protecting group;

it being understood that when the at least one entity contains at least one cationic part, it is associated with at least one anionic counterion allowing the at least one entity to achieve electroneutrality.

2. The at least one fluorescent entity according to claim 1, wherein at least one of $R_f$ and $R'_f$ represents an imidazolium group optionally substituted with a ($C_1$-$C_3$)alkyl group.

3. The at least one fluorescent entity according to claim 1, wherein at least one of $R_f$ and $R'_f$ represents an imidazolyl.

4. The at least one fluorescent entity chosen from those of formulae V and VI according to the claim 1, wherein Y represents a hydrogen atom or an alkali metal.

5. The at least one fluorescent entity chosen from those of formulae (V) and (VI) according to claim 1, wherein Y represents a protecting group.

6. The at least one fluorescent entity chosen from those of formulae (V) and (VI) according to claim 5, wherein Y represents a protecting group chosen from the following radicals:
($C_1$-$C_4$)alkylcarbonyl;
($C_1$-$C_4$)alkylthiocarbonyl;
($C_1$-$C_4$)alkoxycarbonyl;
($C_1$-$C_4$)alkoxythiocarbonyl;
($C_1$-$C_4$)alkylthiothiocarbonyl;
(di)($C_1$-$C_4$)(alkyl)aminocarbonyl;
(di)($C_1$-$C_4$)(alkyl)aminothiocarbonyl;
arylcarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
carboxyl;

$SO_3^-$; $M^+$ with $M^+$ representing an alkali metal;
optionally substituted aryl;
optionally substituted heteroaryl;
optionally cationic, optionally substituted heterocycloalkyl;
isothiouronium —$C(NR^{'c}R^{'d})$=$N^+R^{'e}R^{'f}$; $An^-$ with $R^{'c}$, $R^{'d}$, $R^{'e}$ and $R^{'f}$, which may be identical or different, representing a hydrogen atom or an alkyl group; and $An^-$ represents an anionic counterion;
isothiourea —$C(NR^{'c}R^{'d})$=$NR^{'e}$; wherein $R^{'c}$, $R^{'d}$ and $R^{'e}$, which may be identical or different, represent a hydrogen atom or an alkyl group;
optionally substituted (di)arylalkyl;
optionally substituted (di)heteroarylalkyl;
$CR^{'1}R^{'2}R^{'3}$ with $R^{'1}$, $R^{'2}$ and $R^{'3}$, which may be identical or different, representing a halogen atom or a group chosen from:
alkyl;
alkoxy;
optionally substituted aryl; and
optionally substituted heteroaryl;
$P(Z^1)R^{''1}R^{''2}R^{''3}$ with $R^{''1}$ and $R^{''2}$, which may be identical or different, representing a hydroxyl, alkoxy or alkyl group, $R^{''3}$ representing a hydroxyl or alkoxy group and $Z^1$ representing an oxygen or sulphur atom;
a sterically hindered cyclic group; and
optionally substituted alkoxyalkyl.

7. At least one fluorescent entity according to claim 1, wherein Y represents an alkali metal or a protecting group chosen from:
($C_1$-$C_4$)alkylcarbonyl;
arylcarbonyl;
($C_1$-$C_4$)alkoxycarbonyl;
aryloxycarbonyl;
aryl($C_1$-$C_4$)alkoxycarbonyl;
(di)($C_1$-$C_4$)(alkyl)aminocarbonyl;
($C_1$-$C_4$)(alkyl)arylaminocarbonyl;
optionally substituted aryl;
5- or 6-membered monocyclic heteroaryl;
8- to 11-membered cationic bicyclic heteroaryl;
cationic heterocycle of formula:

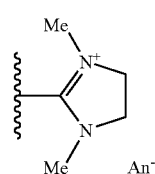

isothiuronium —$C(NH_2)$=$N^+H_2$; $An^-$;
isothiurea —$C(NH_2)$=NH; and
$SO_3^-$, $M^+$ with $M^+$ representing an alkali metal.

8. The at least one fluorescent entity according to claim 6, wherein at least one of $R^{'c}$, $R^{'d}$, $R^{'e}$ and $R^{'f}$ represent a hydrogen atom.

9. The at least one fluorescent entity according to claim 1, chosen from those of formulae 1-25:

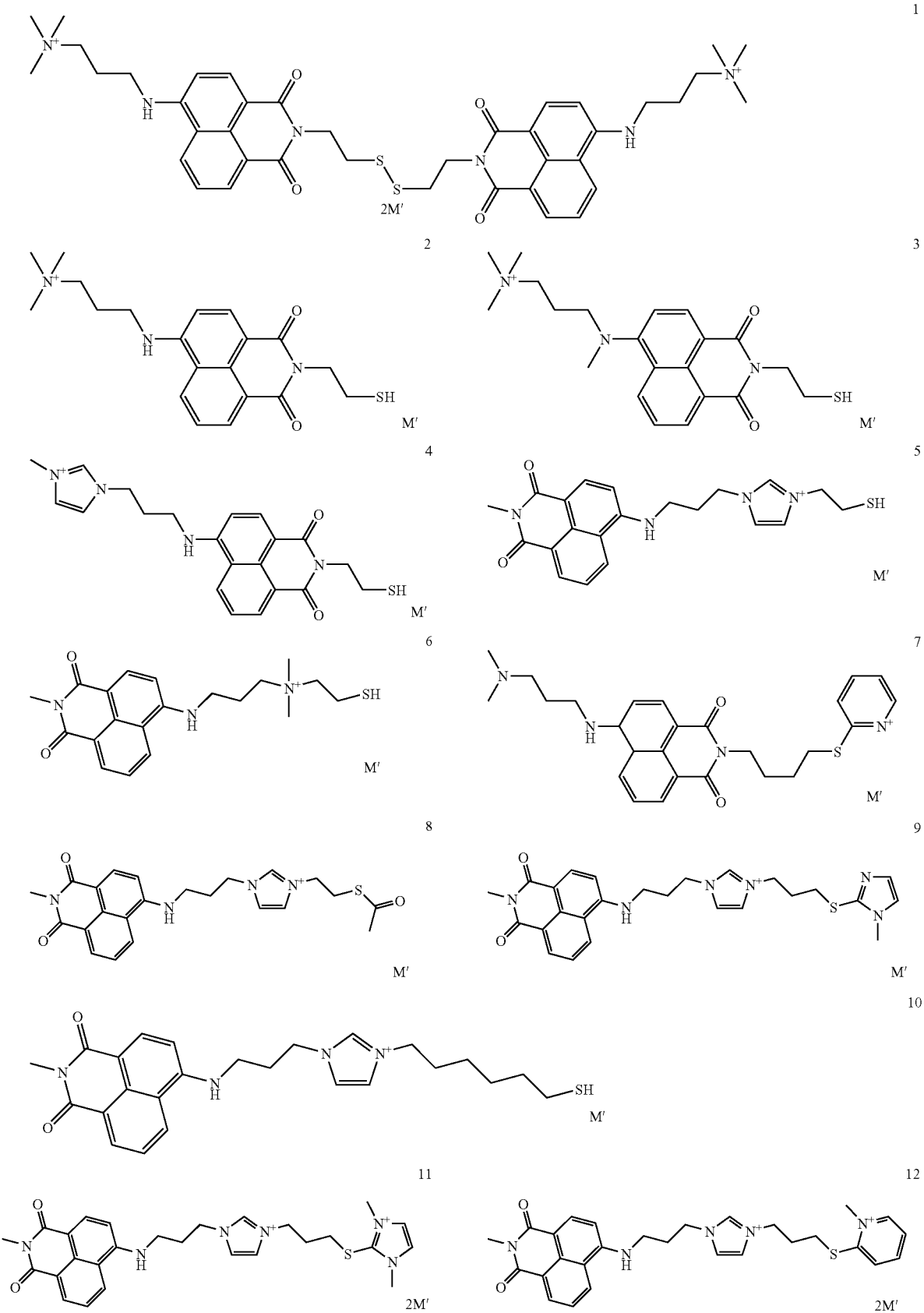

-continued
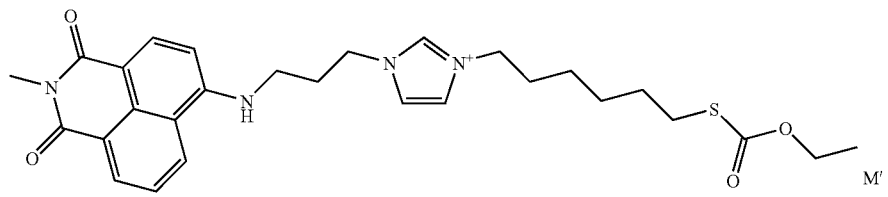
13
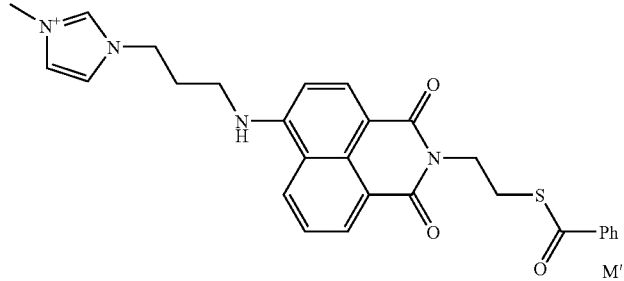
14
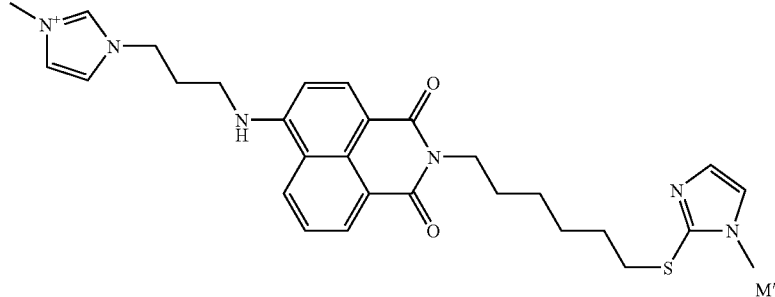
15
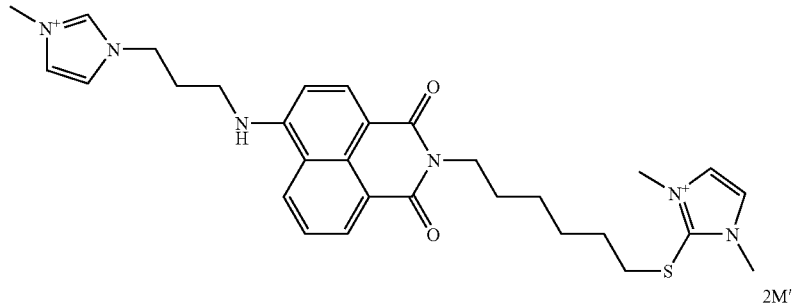
16
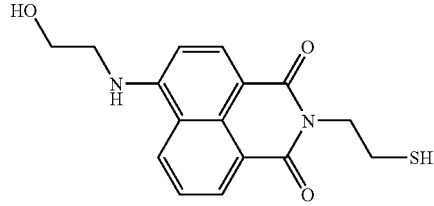
17
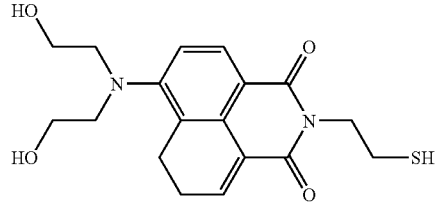
18
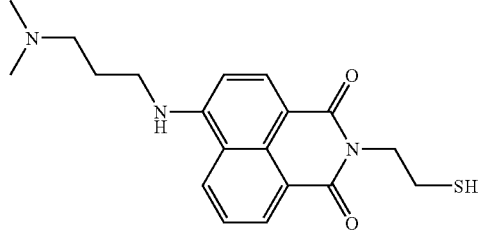
19
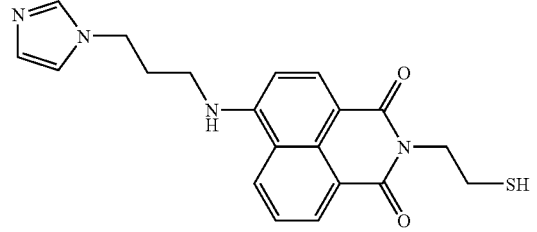
20

-continued
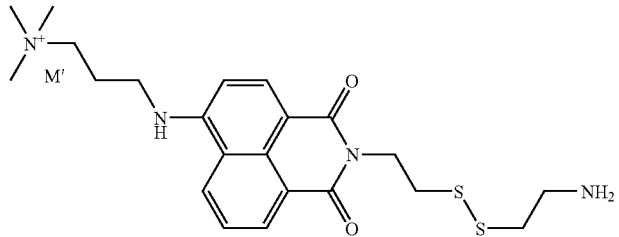
21
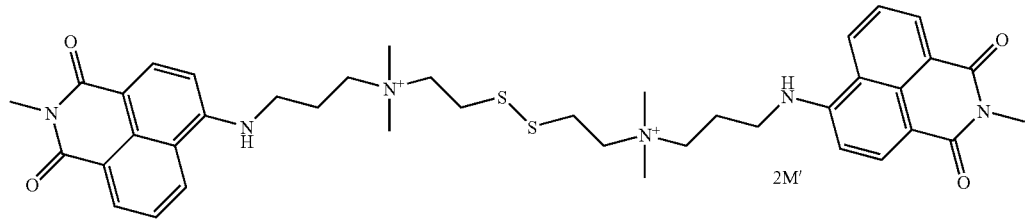
22
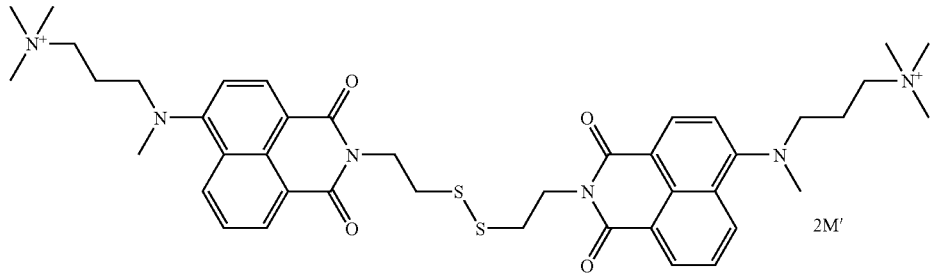
23
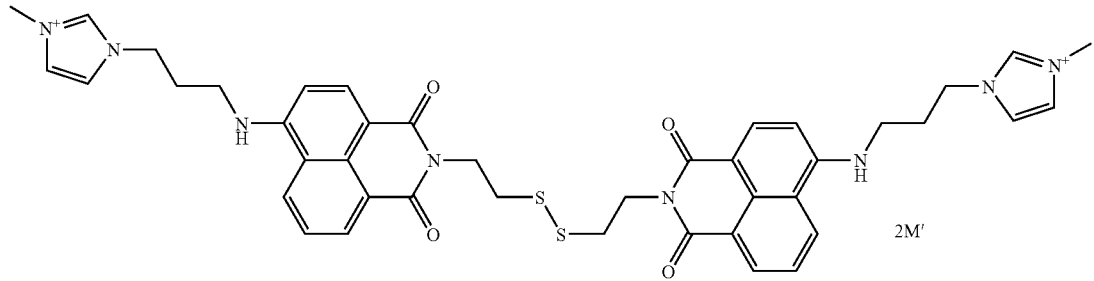
24
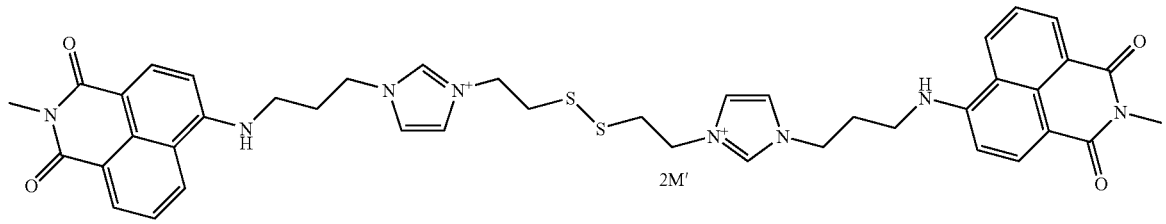
25 wherein M', which may be identical or different, represents an anionic counterion.

10. A dye composition comprising, in a suitable cosmetic medium, at least one fluorescent entity chosen from those of formulae (I), (II), (III), (IV), (V), and (VI):

a (di)($C_1$-$C_4$)(alkyl)amino group, it being possible for said alkyl radicals to form, with the nitrogen atom which bears them, a heterocycle comprising from 5 to 7 members, optionally comprising another heteroatom which may or may not be different from nitrogen;

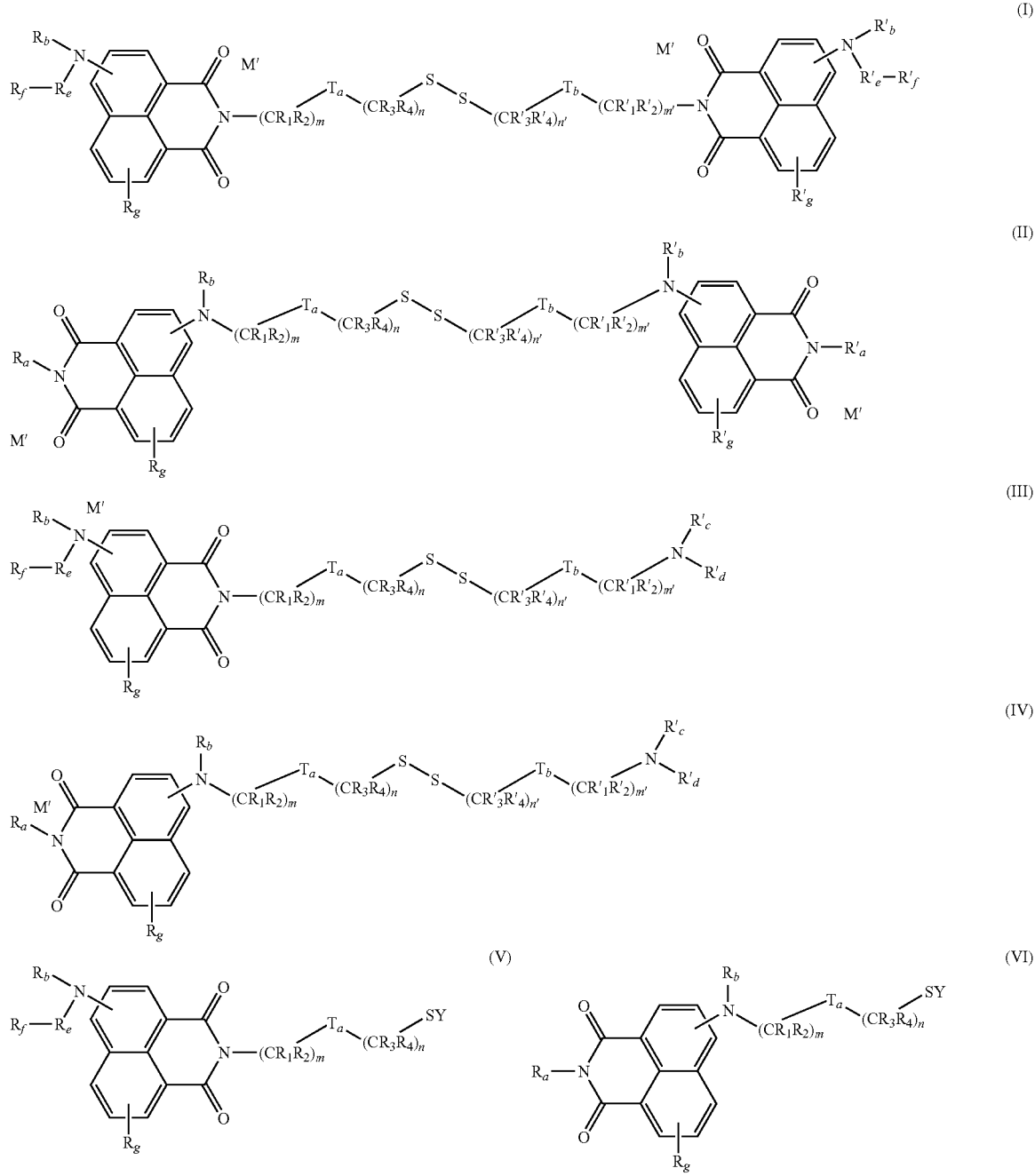

the organic and mineral acid salts, optical isomers and geometrical isomers, and the solvates thereof;
wherein:
$R_a$ and $R'_a$, which may be identical or different, represent an aryl($C_1$-$C_4$)alkyl group or a ($C_1$-$C_6$)alkyl group optionally substituted with a hydroxyl group or $R_b$ and $R'_b$, which may be identical or different, represent a hydrogen atom, an aryl($C_1$-$C_4$)alkyl group or a ($C_1$-$C_6$)alkyl group which is optionally substituted;

$R'_c$ and $R'_d$, which may be identical or different, represent a hydrogen atom, an aryl($C_1$-$C_4$)alkyl group or a $C_1$-$C_6$ alkyl group which is optionally substituted;

$R_e$ and $R'_e$, which may be identical or different, represent an optionally unsaturated, linear or branched, divalent ($C_1$-$C_6$)alkylenyl hydrocarbon-based chain;

$R_f$ and $R'_f$, which may be identical or different, represent i) a quaternary ammonium group $(R')(R''')(R'''')N^+$—, $M'$ where $R''$, $R'''$ and $R''''$, which may be identical or different, represent a hydrogen atom or a ($C_1$-$C_4$)alkyl group, or else $(R'')(R''')(R'''')N^+$— represents an optionally substituted, cationic heteroaryl group, and $M'$ represents an anionic counterion; ii) a hydroxyl group; iii) ($C_1$-$C_6$)(di)(alkyl)amino; or iv) an optionally substituted, noncationic heteroaryl;

$R_g$ and $R'_g$, which may be identical or different, represent a hydrogen or halogen atom, an amino, (di)($C_1$-$C_4$)alkylamino, cyano, carboxyl, hydroxyl, trifluoromethyl, acylamino, $C_1$-$C_4$ alkoxy, $C_2$-$C_4$ (poly)hydroxyalkoxy, ($C_1$-$C_4$)alkylcarbonyloxy ($C_1$-$C_4$) alkoxycarbonyl, ($C_1$-$C_4$)alkylcarbonylamino, acylamino, carbamoyl or ($C_1$-$C_4$)alkylsulphonylamino group, an aminosulphonyl radical, or a ($C_1$-$C_{16}$)alkyl radical optionally substituted with a group chosen from ($C_1$-$C_{12}$)alkoxy, hydroxyl, cyano, carboxyl, amino and (di)($C_1$-$C_4$)alkylamino, or else the two alkyl radicals borne by the nitrogen atom of the amino group form a heterocycle comprising from 5 to 7 members and optionally comprising another heteroatom identical to or different from that of the nitrogen atom;

$R_1$, $R'_1$, $R_2$, $R'_2$, $R_3$, $R'_3$, $R_4$ and $R'_4$, which may be identical or different, represent a hydrogen atom or a ($C_1$-$C_4$)alkyl, ($C_1$-$C_4$)alkoxy, hydroxyl, cyano, carboxyl or (di)($C_1$-$C_4$)(alkyl)amino group, it being possible for said alkyl radicals to form, with the nitrogen atom which bears them, a heterocycle comprising from 5 to 7 members, optionally comprising another heteroatom which may or may not be different from nitrogen;

$T_a$ and $T_b$, which may be identical or different, represent:
i) a σ covalent bond,
ii) at least one radical chosen from —$SO_2$—, —O—, —S—, —N(R)—, —$N^+(R)(R^o)$— and —C(O)—, with R and $R^o$, which may be identical or different, representing a hydrogen atom, a $C_1$-$C_4$ alkyl radical, a $C_1$-$C_4$ hydroxyalkyl radical or an aryl($C_1$-$C_4$) alkyl; or
iii) a monocyclic, cationic or noncationic, heterocycloalkyl or heteroaryl radical comprising two heteroatoms;

m, m', n and n', which may be identical or different, represent an integer ranging from 0 to 6, wherein the sums m+n and m'+n', which may be identical or different, represent an integer ranging from 1 to 10; and >Y represents: i) a hydrogen atom; ii) an alkali metal; iii) an alkaline earth metal; iv) an ammonium group: $N^+R^\alpha R^\beta R^\gamma R^\delta$ or a phosphonium group: $P^+R^\alpha R^\beta R^\gamma R^\delta$ with $R^\alpha$, $R^\beta$, $R^\gamma$ and $R^\delta$, which may be identical or different, representing a hydrogen atom or a ($C_1$-$C_4$)alkyl group; or v) a thiol-function-protecting group;

it being understood that when the at least one entity contains at least one cationic part, it is associated with at least one anionic counterion allowing the at least one entity to achieve electroneutrality.

11. The dye composition of claim 10, further comprising at least one reducing agent.

12. The dye composition according to claim 11, wherein the at least one reducing agent is chosen from: cysteine, homocysteine, thiolactic acid, and salts thereof; phosphines; bisulphite; sulphites; thioglycolic acid and thioglycolic acid esters; borohydrides and derivatives thereof; sodium salts, lithium salts, potassium salts, calcium salts, quaternary ammonium salts; and catechol borane.

13. The dye composition according to claim 10, wherein the at least one fluorescent entity is present in an amount ranging from 0.001% to 50% by weight, relative to the total weight of the composition.

14. A process for dyeing keratin materials, comprising applying to the keratin materials at least one dye composition comprising, in a suitable cosmetic medium, at least one fluorescent entity chosen from those of formulae (I), (II), (III), (IV), (V), and (VI):

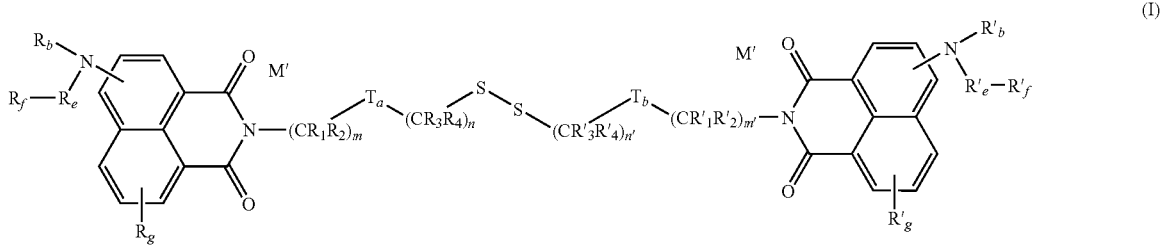

(I)

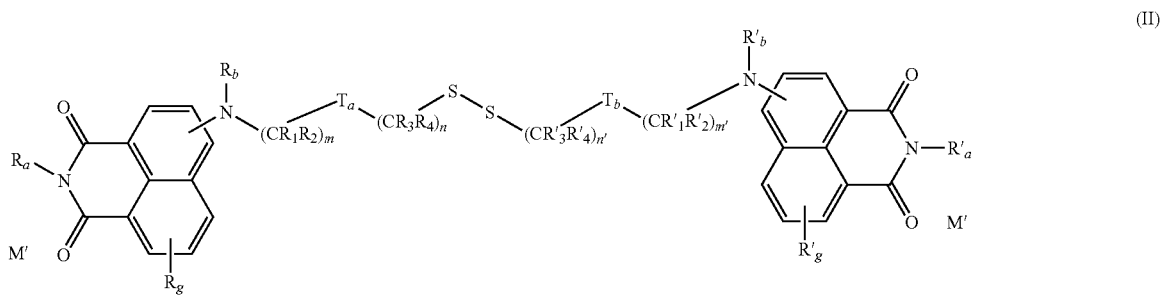

(II)

-continued

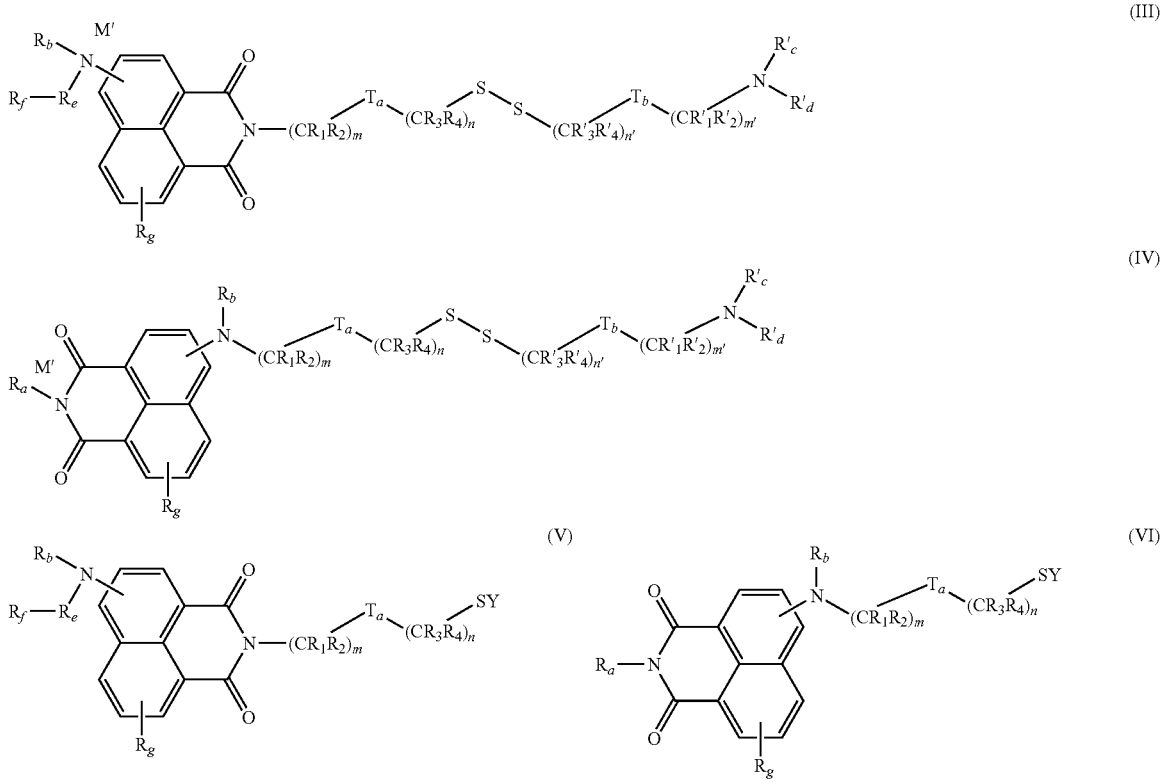

the organic and mineral acid salts, optical isomers and geometrical isomers, and the solvates thereof;
wherein:
- $R_a$ and $R'_a$, which may be identical or different, represent an aryl($C_1$-$C_4$)alkyl group or a ($C_1$-$C_6$)alkyl group optionally substituted with a hydroxyl group or a (di)($C_1$-$C_4$)(alkyl)amino group, it being possible for said alkyl radicals to form, with the nitrogen atom which bears them, a heterocycle comprising from 5 to 7 members, optionally comprising another heteroatom which may or may not be different from nitrogen;
- $R_b$ and $R'b$, which may be identical or different, represent a hydrogen atom, an aryl($C_1$-$C_4$)alkyl group or a ($C_1$-$C_6$)alkyl group which is optionally substituted;
- $R'_c$ and $R'_d$, which may be identical or different, represent a hydrogen atom, an aryl($C_1$-$C_4$)alkyl group or a $C_1$-$C_6$ alkyl group which is optionally substituted;
- $R_e$ and $R'_e$, which may be identical or different, represent an optionally unsaturated, linear or branched, divalent ($C_1$-$C_6$)alkylenyl hydrocarbon-based chain;
- $R_f$ and $R'_f$, which may be identical or different, represent i) a quaternary ammonium group (R")(R'")(R"") $N^+$—, $M'$ where R", R'" and R"", which may be identical or different, represent a hydrogen atom or a ($C_1$-$C_4$)alkyl group, or else (R")(R'")(R"")$N^+$— represents an optionally substituted, cationic heteroaryl group, and $M'$ represents an anionic counterion; ii) a hydroxyl group; iii) ($C_1$-$C_6$)(di)(alkyl)amino; or iv) an optionally substituted, noncationic heteroaryl;
- $R_g$ and $R'_g$, which may be identical or different, represent a hydrogen or halogen atom, an amino, (di)($C_1$-$C_4$)alkylamino, cyano, carboxyl, hydroxyl, trifluoromethyl, acylamino, $C_1$-$C_4$ alkoxy, $C_2$-$C_4$ (poly)hydroxyalkoxy, ($C_1$-$C_4$)alkylcarbonyloxy ($C_1$-$C_4$) alkoxycarbonyl, ($C_1$-$C_4$)alkylcarbonylamino, acylamino, carbamoyl or ($C_1$-$C_4$)alkylsulphonylamino group, an aminosulphonyl radical, or a ($C_1$-$C_{16}$)alkyl radical optionally substituted with a group chosen from ($C_1$-$C_{12}$)alkoxy, hydroxyl, cyano, carboxyl, amino and (di)($C_1$-$C_4$)alkylamino, or else the two alkyl radicals borne by the nitrogen atom of the amino group form a heterocycle comprising from 5 to 7 members and optionally comprising another heteroatom identical to or different from that of the nitrogen atom;
- $R_1$, $R'_1$, $R_2$, $R'_2$, $R_3$, $R'_3$, $R_4$ and $R'_4$, which may be identical or different, represent a hydrogen atom or a ($C_1$-$C_4$)alkyl, ($C_1$-$C_4$)alkoxy, hydroxyl, cyano, carboxyl or (di)($C_1$-$C_4$)(alkyl)amino group, it being possible for said alkyl radicals to form, with the nitrogen atom which bears them, a heterocycle comprising from 5 to 7 members, optionally comprising another heteroatom which may or may not be different from nitrogen;
- $T_a$ and $T_b$, which may be identical or different, represent:
  i) a σ covalent bond,
  ii) at least one radical chosen from —$SO_2$—, —O—, —S—, —N(R)—, —$N^+$(R)(R°)— and —C(O)—, with R and R°, which may be identical or different, representing a hydrogen atom, a $C_1$-$C_4$ alkyl radical, a $C_1$-$C_4$ hydroxyalkyl radical or an aryl($C_1$-$C_4$) alkyl; or
  iii) a monocyclic, cationic or noncationic, heterocycloalkyl or heteroaryl radical comprising two heteroatoms;

m, m', n and n', which may be identical or different, represent an integer ranging from 0 to 6, wherein the sums m+n and m'+n', which may be identical or different, represent an integer ranging from 1 to 10; and Y represents: i) a hydrogen atom; ii) an alkali metal; iii) an alkaline earth metal; iv) an ammonium group: $N^+R^\alpha R^\beta R^\gamma R^\delta$ or a phosphonium group: $P^+R^\alpha R^\beta R_\gamma R^\delta$ with $R^\alpha$, $R^\beta$, $R^\gamma$ and $R^\delta$, which may be identical or different, representing a hydrogen atom or a $(C_1\text{-}C_4)$ alkyl group; or v) a thiol-function-protecting group;

it being understood that when the at least one entity contains at least one cationic part, it is associated with at least one anionic counterion allowing the at least one entity to achieve electroneutrality, and optionally applying at least one reducing agent.

15. The dyeing process according to claim 14, wherein, when the thiol fluorescent entity of formula (V) or (VI) comprises a protecting group Y, the application is preceded by a deprotection step.

16. The dyeing process according to claim 14, wherein the keratin materials are dark keratin fibers having a tone height of less than or equal to 6.

17. The dyeing process according to claim 14, comprising applying the at least one reducing agent before or after applying the at least one fluorescent entity.

18. The dyeing process according to claim 14, comprising simultaneously applying the at least one fluorescent entity and the at least one reducing agent.

19. The dyeing process according to claim 14, wherein the composition further comprises at least one oxidizing agent.

20. The dyeing process according to claim 14, further comprising applying at least one oxidizing agent to the keratin fibres.

21. A multicompartment device comprising:
at least one first compartment comprising a dye composition comprising at least one fluorescent entity chosen from those of formulae (I), (II), (III), (IV), (V), and (VI):

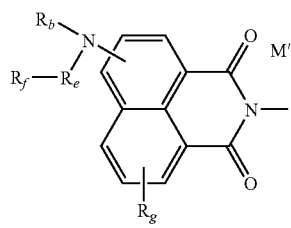
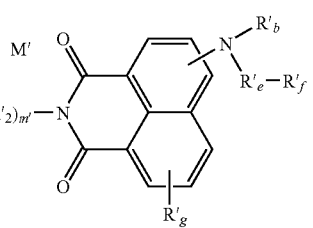
(I)

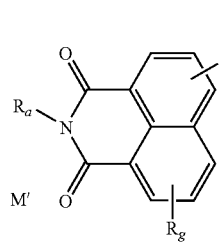
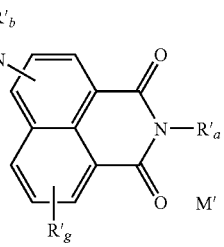
(II)

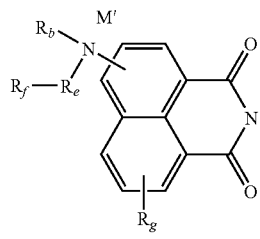
(III)

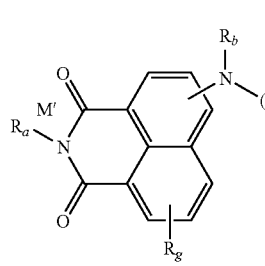
(IV)

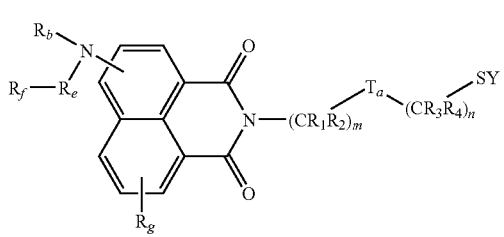 (V)

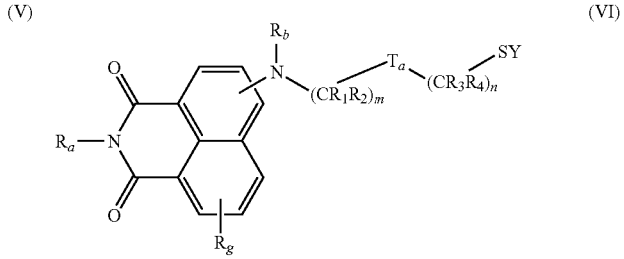 (VI)

the organic and mineral acid salts, optical isomers and geometrical isomers, and the solvates thereof;

wherein:

$R_a$ and $R'_a$, which may be identical or different, represent an aryl($C_1$-$C_4$)alkyl group or a ($C_1$—$C_6$)alkyl group optionally substituted with a hydroxyl group or a (di)($C_1$-$C_4$)(alkyl)amino group, it being possible for said alkyl radicals to form, with the nitrogen atom which bears them, a heterocycle comprising from 5 to 7 members, optionally comprising another heteroatom which may or may not be different from nitrogen;

$R_b$ and $R'_b$, which may be identical or different, represent a hydrogen atom, an aryl($C_1$-$C_4$)alkyl group or a ($C_1$-$C_6$)alkyl group which is optionally substituted;

$R'_c$ and $R'_d$, which may be identical or different, represent a hydrogen atom, an aryl($C_1$-$C_4$)alkyl group or a $C_1$-$C_6$ alkyl group which is optionally substituted;

$R_e$ and $R'_e$, which may be identical or different, represent an optionally unsaturated, linear or branched, divalent ($C_1$-$C_6$)alkylenyl hydrocarbon-based chain;

$R_f$ and $R'_f$, which may be identical or different, represent i) a quaternary ammonium group (R")(R''')(R'''')N$^+$, M' where R", R''' and R'''', which may be identical or different, represent a hydrogen atom or a ($C_1$-$C_4$)alkyl group, or else (R")(R''')(R'''')N$^+$— represents an optionally substituted, cationic heteroaryl group, and M' represents an anionic counterion; ii) a hydroxyl group; iii) ($C_1$-$C_6$)(di)(alkyl)amino; or iv) an optionally substituted, noncationic heteroaryl;

$R_g$ and $R'_g$, which may be identical or different, represent a hydrogen or halogen atom, an amino, (di)($C_1$-$C_4$)alkylamino, cyano, carboxyl, hydroxyl, trifluoromethyl, acylamino, $C_1$-$C_4$ alkoxy, $C_2$-$C_4$ (poly)hydroxyalkoxy, ($C_1$-$C_4$)alkylcarbonyloxy ($C_1$-$C_4$) alkoxycarbonyl, ($C_1$-$C_4$)alkylcarbonylamino, acylamino, carbamoyl or ($C_1$-$C_4$)alkylsulphonylamino group, an aminosulphonyl radical, or a ($C_1$-$C_{16}$)alkyl radical optionally substituted with a group chosen from ($C_1$-$C_{12}$)alkoxy, hydroxyl, cyano, carboxyl, amino and (di)($C_1$-$C_4$)alkylamino, or else the two alkyl radicals borne by the nitrogen atom of the amino group form a heterocycle comprising from 5 to 7 members and optionally comprising another heteroatom identical to or different from that of the nitrogen atom;

$R'_1$, $R_2$, $R'_2$, $R_3$, $R'_3$, $R_4$ and $R'_4$, which may be identical or different, represent a hydrogen atom or a ($C_1$-$C_4$) alkyl, ($C_1$-$C_4$)alkoxy, hydroxyl, cyano, carboxyl or (di)($C_1$-$C_4$)(alkyl)amino group, it being possible for said alkyl radicals to form, with the nitrogen atom which bears them, a heterocycle comprising from 5 to 7 members, optionally comprising another heteroatom which may or may not be different from nitrogen;

$T_a$ and $T_b$, which may be identical or different, represent:

i) a σ covalent bond, ii) at least one radical chosen from —SO$_2$—, —O—, —S—, —N(R)—, —N$^+$(R)(R$^o$)— and —C(O)—, with R and R$^o$, which may be identical or different, representing a hydrogen atom, a $C_1$-$C_4$ alkyl radical, a $C_1$-$C_4$ hydroxyalkyl radical or an aryl($C_1$-$C_4$) alkyl; or iii) a monocyclic, cationic or noncationic, heterocycloalkyl or heteroaryl radical comprising two heteroatoms;

m, m', n and n', which may be identical or different, represent an integer ranging from 0 to 6, wherein the sums m+n and m'+n', which may be identical or different, represent an integer ranging from 1 to 10; and Y represents: i) a hydrogen atom; ii) an alkali metal; iii) an alkaline earth metal; iv) an ammonium group: N$^+$R$^α$R$^β$R$^γ$R$^δ$ or a phosphonium group: P$^+$R$^α$R$^β$R$^γ$R$^δ$ with R$^α$, R$^β$, R$^γ$ and R$^δ$, which may be identical or different, representing a hydrogen atom or a ($C_1$-$C_4$) alkyl group; or v) a thiol-function-protecting group;

it being understood that when the at least one entity contains at least one cationic part, it is associated with at least one anionic counterion allowing the at least one entity to achieve electroneutrality, and at least one second compartment comprising at least one reducing agent.

22. The multicompartment device according to claim 21, comprising at least one third compartment comprising at least one oxidizing agent.

23. A method of lightening dark human keratin fibers, comprising applying to dark human keratin fibers at least one fluorescent entity chosen from those of formulae (I), (II), (III), (IV), (V), and (VI):

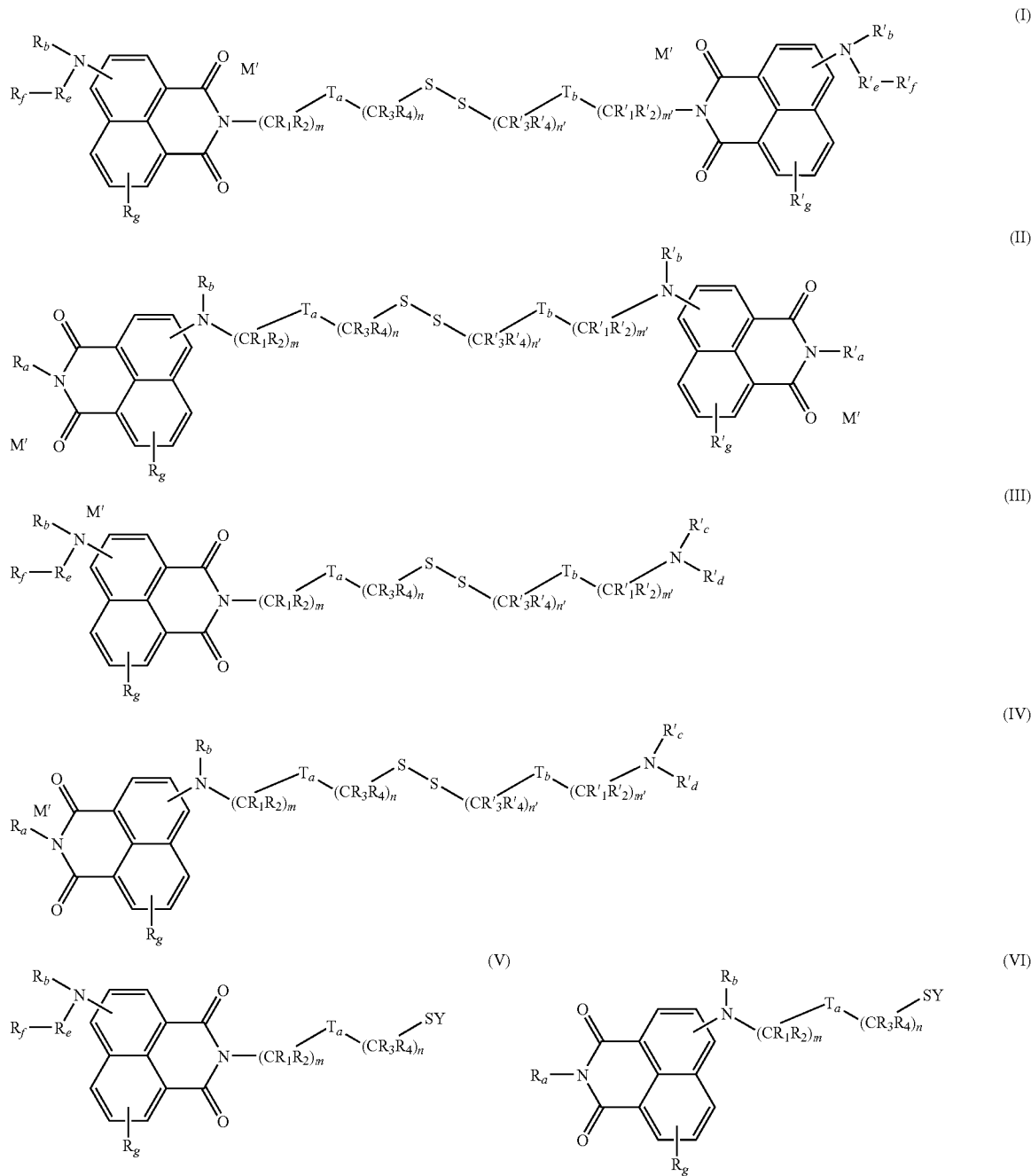

the organic and mineral acid salts, optical isomers and geometrical isomers, and the solvates thereof;
wherein:

$R_a$ and $R'_a$, which may be identical or different, represent an aryl($C_1$-$C_4$)alkyl group or a ($C_1$-$C_6$)alkyl group optionally substituted with a hydroxyl group or a (di)($C_1$-$C_4$)(alkyl)amino group, it being possible for said alkyl radicals to from, with the nitrogen atom which bears them, a heterocycle comprising from 5 to 7 members, optionally comprising another heteroatom which may or may not be different from nitrogen;

$R_b$ and $R'_b$, which may be identical or different, represent a hydrogen atom, an aryl($C_1$-$C_4$)alkyl group or a ($C_1$-$C_6$)alkyl group which is optionally substituted;

$R'_c$ and $R'_d$, which may be identical or different, represent a hydrogen atom, an aryl($C_1$-$C_4$)alkyl group or a $C_1$-$C_6$ alkyl group which is optionally substituted;

$R_e$ and $R'_e$, which may be identical or different, represent an optionally unsaturated, linear or branched, divalent ($C_1$-$C_6$)alkylenyl hydrocarbon-based chain;

$R_f$ and $R'_f$, which may be identical or different, represent
i) a quaternary ammonium group (R")(R''')(R'''') $N^+$—, M' where R", R''' and R'''', which may be identical or different, represent a hydrogen atom or a ($C_1$-$C_4$)alkyl group, or else (R")(R'")(R"")N$^+$— represents an optionally substituted, cationic heteroaryl group, and M' represents an anionic counterion; ii) a hydroxyl group; iii) ($C_1$-$C_6$)(di)(alkyl) amino; or iv) an optionally substituted, noncationic heteroaryl;

$R_g$ and $R'_g$, which may be identical or different, represent a hydrogen or halogen atom, an amino, (di)($C_1$-$C_4$)alkylamino, cyano, carboxyl, hydroxyl, trifluoromethyl, acylamino, $C_1$-$C_4$ alkoxy, $C_2$-$C_4$ (poly) hydroxyalkoxy, ($C_1$-$C_4$)alkylcarbonyloxy ($C_1$-$C_4$) alkoxycarbonyl, ($C_1$-$C_4$)alkylcarbonylamino, acylamino, carbamoyl or ($C_1$-$C_4$)alkylsulphonylamino group, an aminosulphonyl radical, or a ($C_1$-$C_{16}$)alkyl radical optionally substituted with a group chosen from ($C_1$-$C_{12}$)alkoxy, hydroxyl, cyano, carboxyl, amino and (di)($C_1$-$C_4$)alkylamino, or else the two alkyl radicals borne by the nitrogen atom of the amino group form a heterocycle comprising from 5 to 7 members and optionally comprising another heteroatom identical to or different from that of the nitrogen atom;

$R_1$, $R'_1$, $R_2$, $R'_2$, $R_3$, $R'_3$, $R_4$ and $R'_4$, which may be identical or different, represent a hydrogen atom or a ($C_1$-$C_4$)alkyl, ($C_j$-$C_4$)alkoxy, hydroxyl, cyano, carboxyl or (di)($C_1$-$C_4$)(alkyl)amino group, it being possible for said alkyl radicals to form, with the nitrogen atom which bears them, a heterocycle comprising from 5 to 7 members, optionally comprising another heteroatom which may or may not be different from nitrogen;

$T_a$ and $T_b$, which may be identical or different, represent:
i) a σ covalent bond,
ii) at least one radical chosen from —$SO_2$—, —O—, —S—, —N(R)—, —N$^+$(R)(R$^o$)— and —C(O)—, with R and R$^o$, which may be identical or different, representing a hydrogen atom, a $C_1$-$C_4$ alkyl radical, a $C_1$-$C_4$ hydroxyalkyl radical or an aryl($C_1$-$C_4$) alkyl; or
iii) a monocyclic, cationic or noncationic, heterocycloalkyl or heteroaryl radical comprising two heteroatoms;

m, m', n and n', which may be identical or different, represent an integer ranging from 0 to 6, wherein the sums m+n and m'+n', which may be identical or different, represent an integer ranging from 1 to 10; and Y represents: i) a hydrogen atom; ii) an alkali metal; iii) an alkaline earth metal; iv) an ammonium group: N$^+$R$^\alpha$R$^\beta$R$^\gamma$R$^\delta$ or a phosphonium group: P$^+$R$^\alpha$R$^\beta$R$^\gamma$R$^\delta$ with R$^\alpha$, R$^\beta$, R$^\gamma$ and R$^\delta$, which may be identical or different, representing a hydrogen atom or a ($C_1$-$C_4$) alkyl group; or v) a thiol-function-protecting group;

it being and understood that when the at least one entity contains at least one cationic part, it is associated with at least one anionic counterion allowing the at least one entity to achieve electroneutrality, and optionally applying at least one reducing agent.

\* \* \* \* \*

UNITED STATES PATENT AND TRADEMARK OFFICE
CERTIFICATE OF CORRECTION

PATENT NO. : 7,780,743 B2  Page 1 of 5
APPLICATION NO. : 12/293955
DATED : August 24, 2010
INVENTOR(S) : Andrew Greaves et al.

It is certified that error appears in the above-identified patent and that said Letters Patent is hereby corrected as shown below:

In Claim 1, cols. 49-50, formulae I-V:

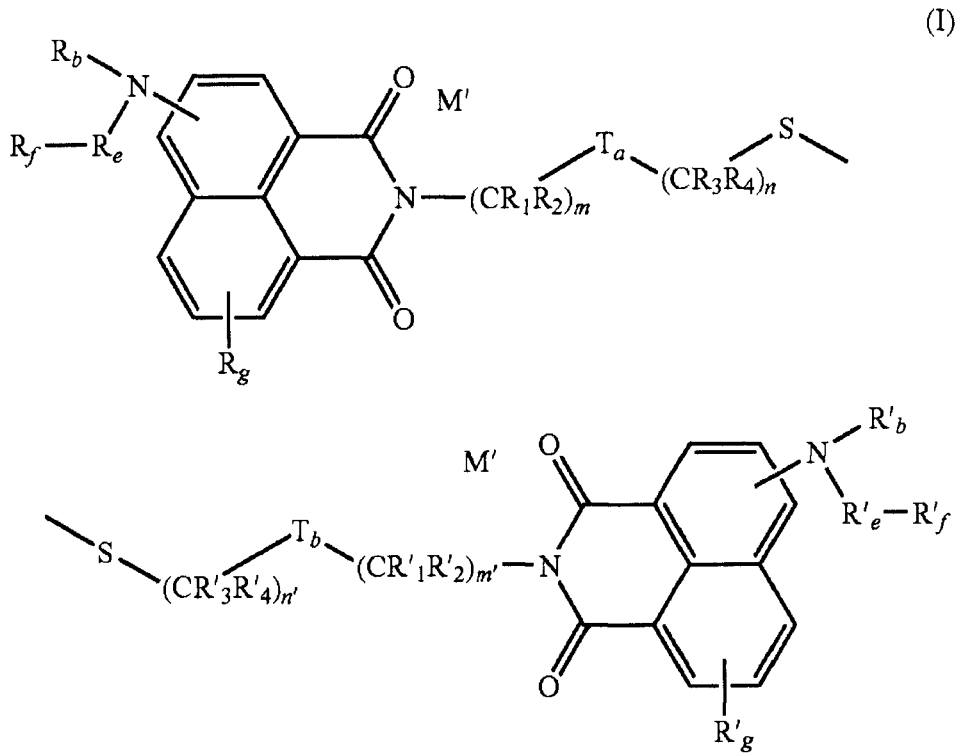

(I)

Signed and Sealed this

Twenty-first Day of December, 2010

David J. Kappos
*Director of the United States Patent and Trademark Office*

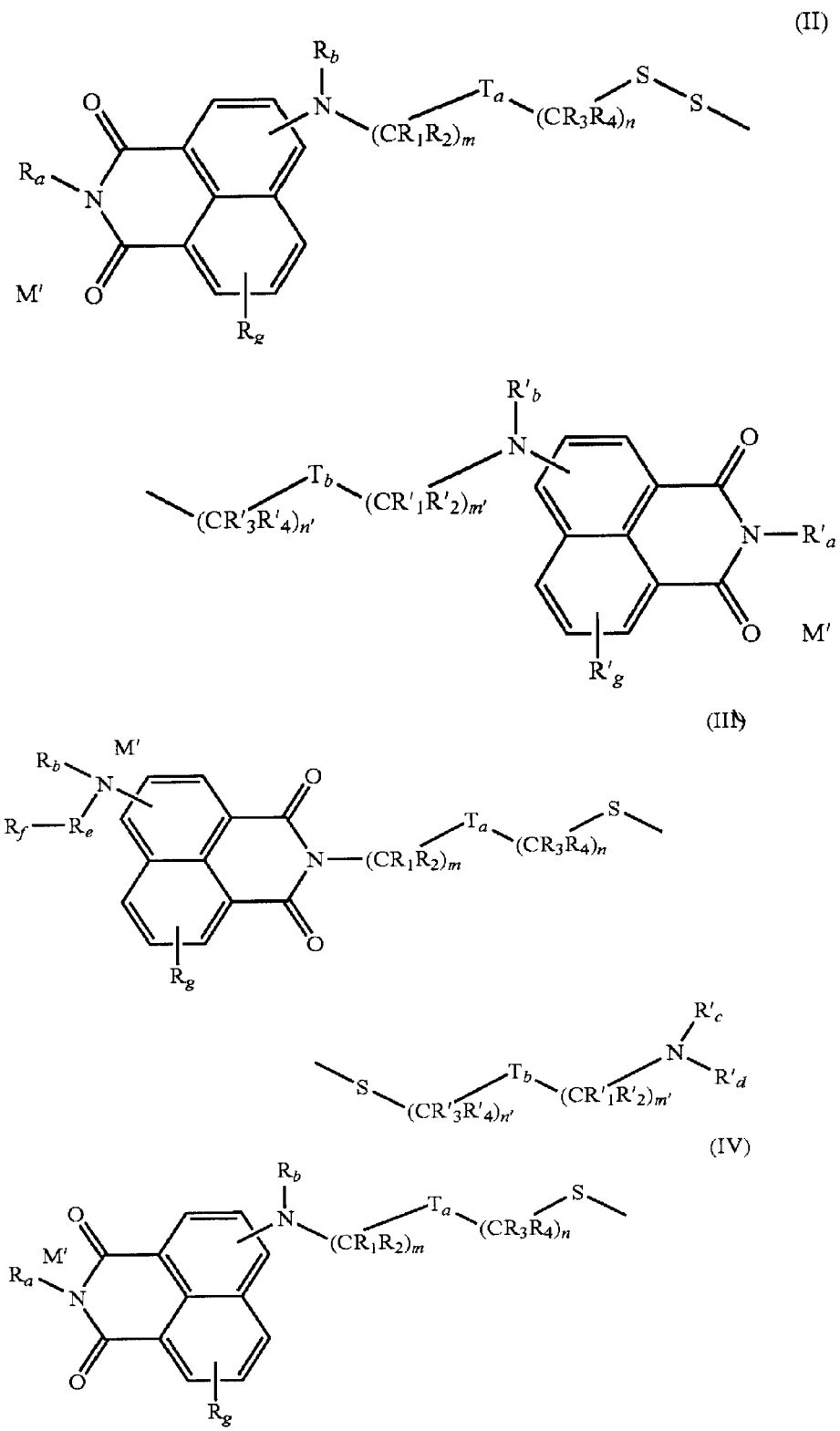

CERTIFICATE OF CORRECTION (continued)
U.S. Pat. No. 7,780,743 B2

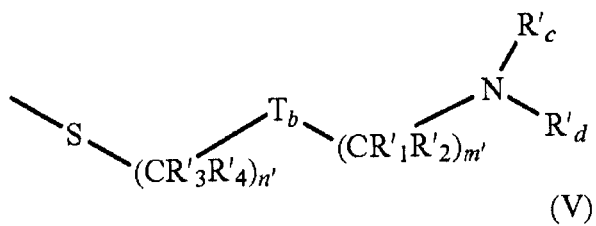

(V)

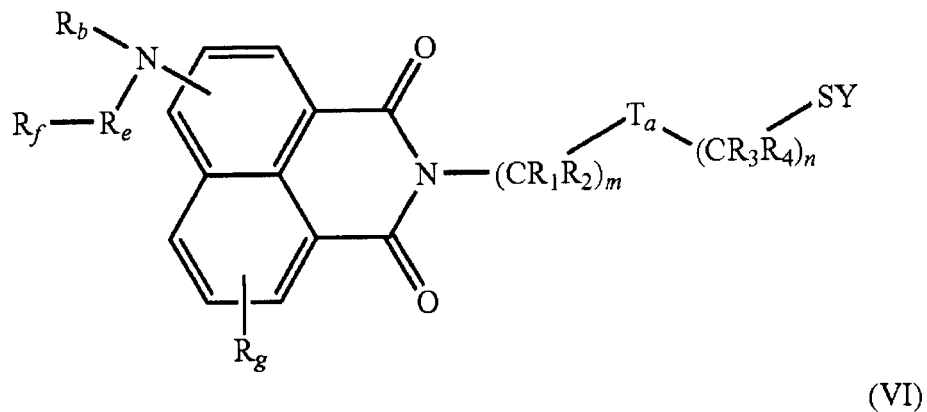

(VI)

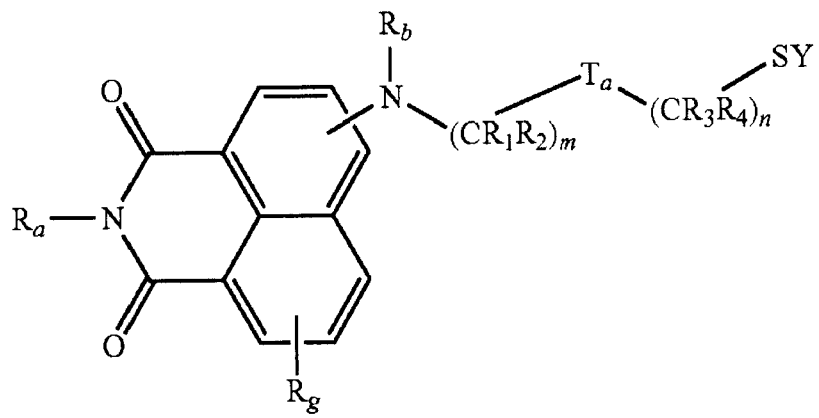

should be depicted as follows:

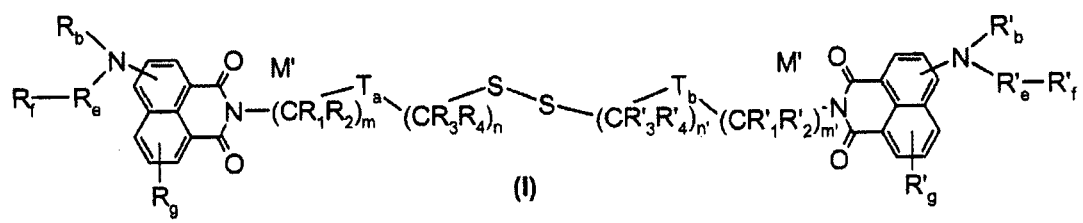
(I)
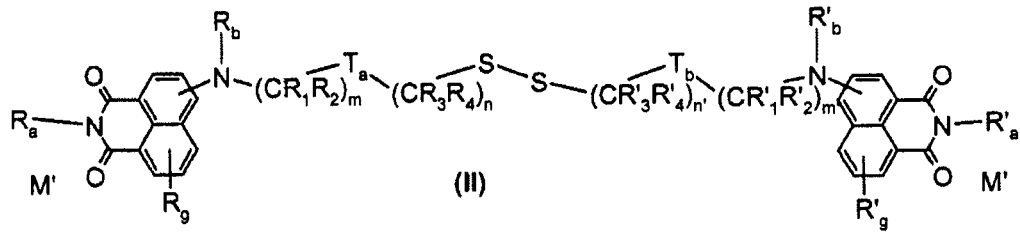
(II)
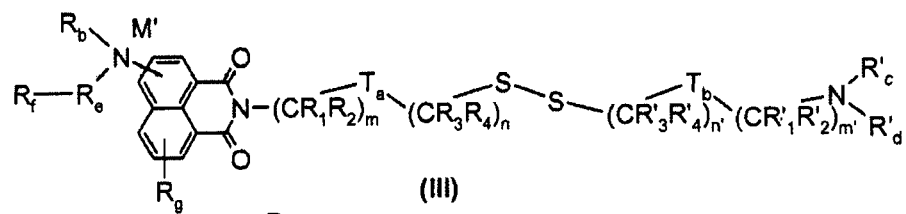
(III)
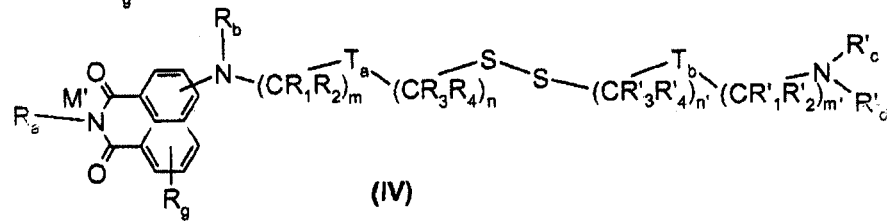
(IV)
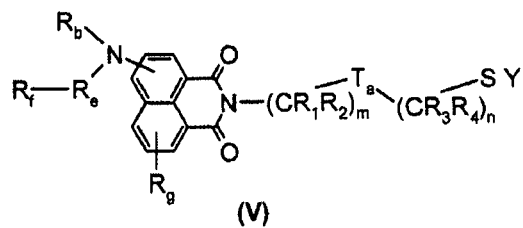
(V)
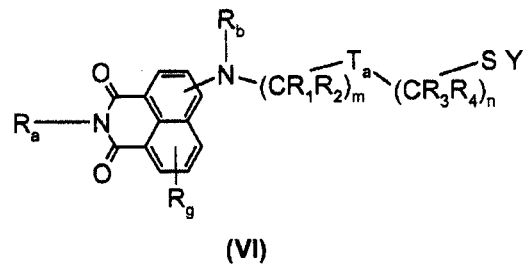
(VI)

In Claim 7, col. 52, line 59, "isothiuronium" should read -- isothiouronium --.

In Claim 7, col. 52, line 60, "isothiurea" should read -- isothiourea --.

In Claim 14, col. 64, line 60, "–$N^+(R)(R^o$ –" should read -- –$N^+(R)(R^o)$– --.

In Claim 21, col. 67, line 22, "($C_j$-$C_6$)" should read -- ($C_1$-$C_6$) --.

In Claim 21, col. 67, line 41, "$N^+$," should read -- $N^+$–, --.

In Claim 23, col. 71, line 27, "($C_j$-$C_4$)" should read -- ($C_1$-$C_4$) --.